US011785908B2

(12) United States Patent
Long

(10) Patent No.: US 11,785,908 B2
(45) Date of Patent: *Oct. 17, 2023

(54) METHODS AND PRODUCTS FOR CONTROLLING SILK FLY AND PHORID FLY IN MAIZE

(71) Applicant: Nature's Best Defense, LLC, Boca Raton, FL (US)

(72) Inventor: Bryant Jerome Long, Wellington, FL (US)

(73) Assignee: Nature's Best Defense, LLC, Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/025,171

(22) Filed: Sep. 18, 2020

(65) Prior Publication Data

US 2021/0204502 A1 Jul. 8, 2021

Related U.S. Application Data

(63) Continuation of application No. 16/096,667, filed as application No. PCT/US2017/064711 on Dec. 5, 2017, now Pat. No. 10,813,312.

(51) Int. Cl.
- *A01H 5/10* (2018.01)
- *A01H 6/46* (2018.01)
- *C12Q 1/6895* (2018.01)

(52) U.S. Cl.
CPC ............. *A01H 6/4684* (2018.05); *A01H 5/10* (2013.01); *C12Q 1/6895* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 5,977,440 | A | 11/1999 | Luthe et al. |
| 8,796,504 | B2 | 8/2014 | Long |
| 8,822,756 | B2 | 9/2014 | Long |
| 8,878,030 | B2 | 11/2014 | Fisher et al. |
| 9,603,321 | B2 | 3/2017 | Goertz et al. |
| 2014/0331348 | A1 | 11/2014 | Long |
| 2015/0113676 | A1 | 4/2015 | Abad et al. |
| 2015/0361447 | A1 | 12/2015 | Beatty et al. |

OTHER PUBLICATIONS

Bernacchi et al. Theor Appl Genet (1998) 97:381-397.*
International Search Report and Written Opinion for PCT Application No. PCT/US2017/064711, dated Mar. 7, 2018.
International Preliminary Report on Patentability for PCT Application No. PCT/US2017/064711, dated Jun. 9, 2020.
Nuessly, G.S., et al.: "Resistance to Spodoptera frugiperda (Lepidoptera: Noctuidae) and Euxesta stigmatias (Diptera: Ulidiidae) in Sweet Corn Derived from Exogenous and Endogenous Genetic Systems," J Con Entomol, Dec. 31, 2007 (Dec. 31, 2007), vol. 100, No. 6, pp. 1887-1895.
Pechan, T. et al., "Insect feeding mobilizes a unique defense protease that disrupts the peritrophic matrix of caterpillars," Proc Natl Acad Sci 99(20):13319-13323 (2002).
Pell, M. et al., Potential Denitrification and Nitrification Tests for Evaluation of Pesticide Effects in Soil, Ambio 27 (1):24-28 (1998).
Pollack, M. et al., "When Cooperation Fails: The International Law and Politics of Genetically Modified Foods," Oxford Univ Press 275 (2009).
Proposals for managing the coexistence of GM, conventional and organic crops, Response to the Dept for Environment, Food and Rural Affairs consultation paper, The Chartered Institute of Environmental Health 1-6 (2006).
"Protesters around the world march against Monsnto," The Associated Press, USA Today 1-2 (2013).
"Public Health Association of Australia: Policy-at-a-glance—Genetically Modified Food Policy," Public Health Assn Australia 1-4 (2007).
"Report 2 of the Council on Science and Public Health: Labeling of Bioengineered Foods," American Medical Association 1-16 (2012).
Roberts TR. Herbicides and Plant Growth Regulators. The Royal Soc Chem. Cambridge, UK: 1998. Metabolic Pathway of Agrichemicals. Part I.
Roberts TR, Hutson DH. Insecticides and Fungicides. The Royal Soc Chem. Cambridge, UK: 1999. Metabolic Pathway of Agrichemicals. Part II.
Santos, A. et al., "Effects of glyphosate on nitrogen fixation of free-living heterotropic bacteria," Lett Appl Microbiol 20:349-352 (1995).
Savonen, C., "Soil microorganisms object of new OSU service," Good Fruit Grower, Oregon State Univ 1-3 (1997).
Scully, B.T. et al., "A Rating Scale to Assess Damage Caused by the Corn Silk Fly (*Euxesta stigmatias* Loew) (Diptera: Otitidae) on the Ears of Sweet Corn," Subtrop Plant Sci 54:34-38 (2002).
Scully, B.T. et al., "Resistance in Maize to Euxesta stigmatias Loew (Diptera: Otitidae)," J Entomol Sci 35 (4):432-443 (2000).
Srinidi, M. et al., "A Naturally Occurring Plant Cysteine Protease Possesses Remarkable Toxicity against Insect Pests and Synergizes Bacillus thuringiensis Toxin," PloS One 3(3):1-7 (2008).

(Continued)

*Primary Examiner* — Medina A Ibrahim
(74) *Attorney, Agent, or Firm* — Locke Lord LLP; Keith Parr; Smitha Uthaman

(57) ABSTRACT

The invention relates to methods for producing maize plants, plant materials and seeds that provide a means of controlling and defending against the corn silk fly and phorid fly, and improved maize plants, plant materials and seed produced by these methods. Corn silk flies and phorid flies are highly detrimental and destructive insects damaging maize plants, plant materials and seed during their growing stages in many different geographic regions worldwide. The inventive methods utilize molecular markers to incorporate genes that prove a means for controlling and defending against the corn silk fly and phorid fly into male and female inbred parent maize lines used to produce maize hybrids, or into at least one of the maize parent lines of a hybrid.

6 Claims, 2 Drawing Sheets

Specification includes a Sequence Listing.

(56) References Cited

OTHER PUBLICATIONS

"Statement on Genetically Modified Organisms in the Environment and the Marketplace," Canadian Assn of Physicians for the Environment 1-2 (2013).
Steyskal, G.C. et al., "A Catalogue of the Diptera of the Americas: South of the United States," Depto Zoologia Secretaria da Agr, Sao Paulo, Brasil 54.1-54.31 (1968).
Stone, A. et al., "A Catalog of the Diptera of America: North of Mexico," US Dept of Agr, Washington, DC 642-654 (1965).
Sudermann, H., "Genetically Altered Wheat Flagged; Thailand Detects Shipment Not Cleared for Commercial Sales," Spokesman Review (Spokan, WA) (1999).
Tabashnik, B. et al., "Insect resistance to Bt crops: evidence verus theory," Nature Biotechnology 26(2):199-202 (2008).
Teetes, G., "Plant Resistance to Insects: A Fundamental Component of IPM," IPM World Textbook, Univ of Minn, St Paul, MN 1-8 (2013).
Van Eenennamm, A et al., "The Potential Impacts of Mandatory Labeling for Genetically Engineered Food in the United States," Council for Agricultural Science and Technology 54:1-16 (2014).
Waltz, E., "Battlefield," Nature 461:27-32 (2009).
Wang, P. et al., "An intestinal mucin is the target substrate for a baculovirus enhancing," Proc Natl Acad Sci USA 94:6977-6982 (1997).
Wang, P. et al., "Molecular Cloning and Sequencing of a Novel Invertebrate Intestinal Mucin cDNA," J Biol Chem 272 (26):16663-16669 (1997).
Warren, G.F., "Spectacular Increases in Crop Yields in the United States in the Twentieth Century," Weed Tech 12:752-760 (1998).
Waskom, R., "Best Management Practices for Private Well Protection," Colorado State Univ Cooperative Extension 1-12 (1995).
Webster, J.P.G. et al., "Estimating the economic benefits of alternative pesticide usage scenarios: wheat production in the United Kingdom," Crop Production 18:83-89 (1999).
Widstrom, N.W. et al., "Combining Abilities and Relative Dominance among Maize Inbreds for Resistance to Earworm Injury," Crop Sci 9(2):216-219 (1969).
Widstrom, N.W. et al., "Recurrent Selection for Resistance to Leaf Feeding by Fall Armyworm on Maize," Crop Sci 32:1171-1174 (1992).
Williams, W.P. et al., "Laboratory Bioassay for Resistance in Corn to Fall Armyworm (*Lepidoptera: noctuidae*) and Southwestern Corn Borer (*Lepidoptera: pyralidae*)," J Econ Entomol 83:1578-1581 (1990).
Witkowski, J.F. et al., "Corn Production, Bt corn and European corn borer: Long-term success through resistance management," Univ of Minn Extension 1-15 (2017).
Xia, R., "Hundreds in L.A. march in global protest against Monsanto, GMOs," Los Angeles Times (2013).
Aktar, W. et al., "Impact of pesticides use in agriculture: their benefits and hazards," Interdisc Toxicol 2(1):1-12 (2009).
Anikala, A. et al., "Integration of Ethylene and Jasmonic Acid Signaling Pathways in the Expression of Maize Defense Protein Mir1-CP," Mol Plant Microbe Interact 22(12):1555-1564 (2009).
Barcelo, D. et al., "Pesticides and their Degradation Products: Characteristics, Usage and Environmental Behaviour," Trace Determination of Pesticides and Their Degradation Products in Water, Elsevier, Amsterdam, The Netherlands 3 (1997).
Bjerga, A., "Monsanto Modified Wheat Not Approved by USDA in Field," Bloomberg News 1-3 (2013).
Bortleson, G. et al., "Pesticides is Selected Small Streams in the Puget Sound Basin, 1987-1995," U.S. Geological Survey & Wash State Depart of Ecology 1-4 (1997).
Branco, M.C. et al., "Avaliacao da Resistencia a Helicoverpa zea (Boddie) Lepidoptera: Noctuidea) e *Euxesta* sp. (Diptera: Otitidae) em linhagens de milho-doce," An. Soc. Entomol. Brasil 23:136-140 (1994) (with English-language translation).
Brooks, T. et al., "Genetic Basis of Resistance to Fall Armyworm (*Lepidoptera: noctuidae*) and Southwestern Corn Borer (*Lepidoptera: crambidae*) Leaf-Feeding Damage in Maize," J. Econ. Entomol. 100(4):1470-1475 (2007).
Brouwer, A. et al., "Characterization of Potential Endocrine-Related Health Effects At Low-Dose Levels of Exposure to PCBs," Environ Health Perspect 107(4):639-649 (1999).
Capinera, J.L., Handbook of Vegetable Pests. Academic Press, San Diego 224-227 (2001).
"Contamination Found in Taco Bell Taco Shells, Food Safety Coalition Demands Recall by Taco Bell, Philip Morris," GE Food Alert Coalition Press Release 1-3 (2000).
"Cotton in India," Monsanto 1-2 (2010).
Crisp, T. et al., "Environmental Endocrine Disruption: An Effects Assessment and Analysis," Environ Health Perspect 106(1):11-56 (1998).
Davis, F.M. et al., "Resistance to Multiple *Lepidopterous* Species in Tropical Derived Corn Germplasm," Mis Agri Exp St Tech Bull 157:1-6 (1988).
"Deloitte 2010 Food Survey Genetically Modified Foods," Deloitte Development LLC (2010).
Eddleston, M., "Patterns and problems of deliberate self-poisoning in the developing world," QJ Med 93:715-731 (2000).
Ferry, N. et al., "Plant-insect interactions: molecular approaches to insect resistance," Curr Opin Biotechnol. 15:155-161 (2004).
Ferry, N. et al., "Transgenic plants for insect pest control: a forward looking scientific perspective," Transgenic Res 15:13-19 (2006).
Fulmer, M., "Taco Bell Recalls Shells That Used Bioengineered Corn," L.A.Times. 1-3 (2000).
Gatehouse, A.M.R. et al., "Approaches to insect resistance using transgenic plants," Phil Trans R Soc Lond B 342:279-286 (1993).
"Genetically modified foods and health: a second interim statement," British Medical Association 1-8 (2004).
"Genetically Modified Maize: Doctors' Chamber Warns of 'UnpredictableResults' to Humans," PR Newswire (Jan. 2, 2013).
"Genetically Modified Organisms (GMO): Characteristics of Genetically Modified Organisms," PubH 5103: Exposure to Environmental Hazards, Univ of Minn Environmental Health Sciences 1-3 (2003).
"Genetic Vulnerability of Major Crops," National Academy of Science 70-80, 97-118 (1972).
Glotfelty, D.E. et al., "Volatilization of Pesticides from Soil," Reactions and Movements of Organic Chemicals in Soil, Soil Science Society of America, Inc, Madison, WI 181-207 (1989).
Goyal, G. et al., "Distribution of Picture-Winged Flies (*Diptera: ulidiidae*) Infesting Corn in Florida" Fla Entomol 94 (1):35-47 (2011).
Goyal, G. et al., "Examination of the Pest Status of Corn-Infesting Ulidiidae (Diptera)," Environ Entomol 41 (5):1131-1138 (2012).
Hallenbeck T., "How GMO labeling came to pass in Vermont," Burlington Free Pres. 1-5 (2014).
Harrison, R.L. et al., "Proteases as Insecticidal Agents," Toxins 2:935-953 (2010).
"Harvest on the Horizon: Future Uses of Agriculture Biotechnology," Pew Initiative on Food and Biotechnology 1-6 (2001).
Hunt, L., "Factors determining the public understanding of GM technologies," AgBiotechNet 6(128):1-8 (2004).
Hurley, P.M. et al., "Mode of Carcinogenic Action of Pesticides Inducing Thyroid Follicular Cell Tumors in Rodents," Environ Health Persp 106(8):437-445 (1998).
"Idea Position on Genetically Modified Foods," Irish Doctors Environmental Assn (2014).
Igbedioh, SD., "Effects of Agricultural Pesticides on Humans, Animals, and Higher Plants in Developing Countries," Arch Environ Health 46(4):218-224 (1991).
Jeyaratnam, J., "Health problems of pesticide usage in the Third World," Br J Ind Med 42:505-506 (1985).
Johnson, N., "The genetically modified food debate: Where do we begin" Grist 1-7 (2013).
Kaskey, J., "DuPont-Dow GM Corn defeated by armyworms," GM Watch 1-3 (2012).
Kole, R.K. et al., "Pesticide Residues in the Aquatic Environment and Their Possible Ecological Hazards," J Inland Fish Soc India 27(2):79-89 (1995).

(56) References Cited

OTHER PUBLICATIONS

Kole, R.K. et al., "Phototransformation of some pesticides," J Indian Chem Soc 76:595-600 (1999).

Kopicki, A., "Strong Support for labeling Modified Foods," The New York Times 1-2 (2013).

Lazarus, R., "The Tragedy of Distrust in the Implementation of Federal Environmental Law," Law and Contemporary Jroblems 54(4):311-74 (1991).

Lopez, L. et al., "Mir1-CP, a novel defense cysteine protease accumulates in maize vascular tissue in response to ierbivory," Planta 226:517-527 (2007).

Majewski, M. et al., "Governing Processes," Pesticides in the Atmosphere: Distribution, Trends, and Governing actors, Ann arbor Press, Inc., Chelsea, MI 118 (1995).

Mao, Y. et al., "Cysteine protease enhances plant-mediated bollworm RNA interference," Plant Mal Biol 83:119-120 (2013).

"March Against Monsanto' Protesters Rally Against U.S. Seed Giant and GMO Products," The Huffington Post (Jan. 3, 2013).

Mitchell, P., "Europe sees sham decline in GMO research," Nature Biotechnology, 21:468-469 (2003).

Mohan S. et al., "Degradation of S. frugiperda peritrophic matrix by an inducible maize cycteine protease," J Ins Physiol 52:21-28 (2006).

Murray, CJL & Lopez, Ad. The global burden of disease: a comprehensive assessment of mortality and disability from diseases, injuries and risk factors in 1990 and projected to 2020 [vol. 1 of 10 in the Global Burden of Disease and Injury Series] Cambridge, MA: Harvard School of Public health (1996).

Nuessly, G. et al., "Cornsilk fly *Euxesta stigmatias*," Univ of Fla Entomol & Nematol 1-14 (2013).

Owens, D. et al., "Cob Flies, *Megaselia* spp. (Diptera: Phoridae), in Sweet Corn," Univ of Fla Entomol & Nematol (Jan. 5, 2016).

Pechan T. et al., "A Unique 33-kD Cysteine Protease Accumulates in Response to Larval Feeding in Maize Genotypes Resistant to Fall Armyworm and Other Lepidoptera," The Plant Cell 12:1031-1040 (2000).

\* cited by examiner

SEQUENCE LISTING

```
<160> NUMBER OF SEQ ID NOS: 12

<210> SEQ ID NO 1
<211> LENGTH: 982
<212> TYPE: DNA
<213> ORGANISM: Zea mays

<400> SEQUENCE: 1
ggaggcggcg gaggcctctc tcccgtcgga gcagggcagg ggttgcgtct cagttcctgg      60
ttgtgttgtt gtaagctccc aggtttcttc tcttcgcgtg agctagctag agtgggatcg     120
```

-continued

```
cgaggaagaa ggatgtcgtg ctgcggaggc aactgcgggt gcggcagcgg atgcaagtgc    180
ggcagcggct gcggagggta agcattgcac cgcactgcac tgccgttctg ttccgttccg    240
ttccgttgcg ttcctccctc ggaatcagat ctgtctctgt gtatgcaggt gcaagatgta    300 cccgacatg gttgagcagg tgaccaccac caccaccacc cagactctca tcatgggtgt     360
tgcgccatcc acgggcgggt tcgaggcggc cgccggagct gagaacggcg ggtgcaagtg    420
cggcgccagc tgcacctgcg acccctgcac ctgcaagtga ggatgaccgg gtgcagcatg    480
caggccgtga cgatggagga agtagctaga tcggaaggac acccttcagt atctctagct    540
aaggccctgt tcaatctccg cgagataaac tttagcagct tttttttagc tacttttagc    600
catttgtaat ctaaacagga gagctaatgg tgataattga aactaaactt tagcacttca    660
attcatatag ctaaagttta gtaggaagct aaagtttatc ccgtgagatt gaaacggggc    720
ctaaatcaag ctctgcagta tgttgtagca gtgtcgtctg tgtttgccgc catgcgcgcg    780
tagctagcta gtggtggtgg taaacgaata attgtcctgt tcttcctcct cctcggcccc    840
tgccagtgtt gcgtcgtgtg ggccggccgg gtgcatgcac agcaccaggc catgcccgct    900
gctctgtgcg cactttttt tttccttcgt gctgtgtctc cattttccat ctatatgcat     960
ccgatttgtg acgtcgtcag ta                                             982
```

<210> SEQ ID NO 2
<211> LENGTH: 1164
<212> TYPE: DNA
<213> ORGANISM: Zea mays

<400> SEQUENCE: 2

```
attccttatt cacggaccaa tcttgtctct actgtcgtcg tcgccagcga tgtcgtctcc     60
atccgagatg cgaggaggag tgaagaaaac caaatctgct acatccttct ttcttctccc    120
tttcctctcc aatccaaatg tactggcatc ctccacctgc aagctgcgca ccgggctacc    180
agacctccat ccatcgcaag cttctagcca ctgaaggcaa attttgttgt gtcacaattg    240
aaggacatgg agcaaaggcc aagaaggat tacaatgcag tgaagaccat cctgtcaaag     300
agtggatttg gttgagacaa tgttctgaag atggtgacca ctatcgatgg tttatggtct    360
gaacttccca gaaaatttgc aaaaaatgta agaacaactc cttccttaat tatgatgagt    420
tgcatgagat ttacaatggt atgatcaagc ccatcctttg tctcttcaat tttatttaat    480
cacgtgttct gctcattggt aaaatagttt atttctttat actcgatacg taatattgtt    540
taagggtagg gaaacactat agaagctttc agagaagtca tgcaaaaccg agaacaaatt    600
tgttgtagat gatcgcggac aaaaataagt acacctagcc caaccattcc tacaaccttc    660
tccatgtgaa attctcgcct agctcgtatc ttatgacctt gggaaatttc ttcaacatgt    720 ttttttcct gaaaggatgg aagtgtgtat atatgggtgt gtccgctcat gagaaggatt     780
tccatcaaac cactttaaa caatctccat ttccttgtca tctctcttct ctttctattg     840
aagaaattcc tccagtacat ttcttcgtgt attcaccggc ctcacagctt gttgcagttg    900
cacacacctt attgtaaatg taccattgaa aacaaagcca aattaatcag ctaggtgatt    960
acataaagaa aaggtataaa ccggtttcta ttcataaatt atagcagact gggcatagta   1020
cctgttgtgt agtactaatc atcacattga ataataact cgcagattgt acacggtata    1080
tatagtgaca gagaggtaag tgagttttgc acttctcttc cttggtcaaa tctgtaatat   1140
taatgggttt caattctgtt ctac                                          1164
```

<210> SEQ ID NO 3
<211> LENGTH: 1763
<212> TYPE: DNA
<213> ORGANISM: Zea mays

<400> SEQUENCE: 3

```
cgaaagccca ccaccacgat ccgcgccaca aaatagtgcg gtgcgcccag ccctgtcggc    60
tcggctgcct ccgcctccgc tccgcgccgc gcatataacc ggaccccagt tccgtgacgg   120
cctcagtcag tccccgagga ggaggaacag ctaggtgcgg aaaggcagct ctcagtctca   180
cactctgcca atcccagcct gagttctgct ctgctctgct tctagccatg gtggcctcgc   240
ggatcttgct cccgctgctg ctctccctct tcctatgctc gcattgctgt accggagcgg   300
cggcggcgaa gcggcagctg ctgcaggcgc agtcgcaggt gaagttcgac ttctccccgt   360
tcctgatcga gtacaagaac gggcgcgtga agcggctgat gggcaccaac gtggtgtccg   420
cgtcgtcgga cgcgctgacg ggcgtcacct cccgcgacgt gaccatcgac gcttcgacgg   480
gcgtcgccgc gcggctctac ctcccgagct tccgcgccag cgcccgggtg ccgtgctcg   540
tctacttcca cggcggcgcg ttcgtggtgg agtcggcgtt cacgcccatc taccacgcct   600
acctcaacac gctggccgcc agggcgggcg tggtggccgt gtcggtgaac taccggctgg   660
cgccggagca cccgctcccg gcggcgtacg acgactcctg gcggcgctc aggtgggtgc   720
tggcgagcgc ggccgggtcg gaccgtggc tggcccagta cggcgacctg ttccgcctgt   780
tcctggccgg cgacagcgcc ggcggcaaca tcgcgcacaa cctggcactg cgcgcggggg   840
aggaaggcct ggacgcggc gcgcggatca agggcgtggc gctgctggac ccctacttcc   900
agggccggag ccccgtgggc gccgagtccg cggacccggc gtacctccag tccgcggcgc   960
gcacctggag cttcatctgc gcggggaggt acccgatcaa ccaccctac gcggacccgc  1020
tcctgctgcc ggcctcctcg tggcagcacc tcggcgcctc ccgcgtgctg gtcaccgtgt  1080
cggggcagga ccgcctcagc ccctggcagc gcgggtacta cgccgcgctc cagggcagcg  1140
gctggcccgg cgaggccgag ctgtacgaga ccccggcga gggccacgtc tacttcctca  1200
ccaagcttgg ctcgccgcag gcgctcgccg agatggccaa gctcgtcgcc ttcattaacc  1260
gcgactagca gccgccggag taaatccggt acatgcaggc cgctgcagtg ccgcgacaac  1320
atcagcatac ctatagtaac tagcgagagc gaggtgattg gtagtggtaa ttacattttt  1380
ttttgggtcc ttgatgatga ttactgtgcg tcggaagaaa agaacggttc ctctctccag  1440
aaacctcgtc cggacggata ggaggggacc ggtgtgttcg cttgcgcggc gttgcgtgtc  1500
attgactgca gtctacaggc taccgtgccg tgcactgtta actgcgtgta gcgcggtact  1560
gccagactgc cagttacagt agtcttcaga gtataatatt ttttagtata gaagcgtcac  1620
tctactaccg acccaatgca tcgtgtaact tttgtggtac tagtgctata tggtggtgat  1680
tttgtcggag tggtcatttt tttccctgt ggcaatcaca tgcgccggcc accgcggtcc  1740
gcggcggaga atgtgtgtct cgt                                         1763
```

<210> SEQ ID NO 4
<211> LENGTH: 4610
<212> TYPE: DNA
<213> ORGANISM: Zea mays

<400> SEQUENCE: 4

```
gtacgagccg cgggccgtgt ccacctttct gttcagcctt gctgtcttgt cgcgcgctct    60
cttcctctcc cgcggccccg ccccacagct ctgctccccc gtccttccga cgttcacact   120
```

```
gccttctctt ctcagccccc acgtcgcgtc ttacaagagg catcgcagcc tccgattccc    180
cgagaggcgg cacgtcggca cggcacgctc ttctcctagc gcgggtggtg tgggtaaccg    240
cggcgcgaga agctgctcga tcttgcagct cgtgccgggc gccggggctg tgcggtgcgg    300
gtgctgcgga catgagctgc ctgtgctggt tcaagcggag gtccaggaaa gggcgatcgt    360
cgtcgtcggg gaagcgaggg gcgtcgtcga cggcgacggt gtcggtgtcg ggccccgcga    420
ccgcgaccgc gaccacgacc acgacggcgt cggcggagag cacgagccgg tcggacgact    480
cgggcgcggt gcggccggtg agcaagtcgg cgggctcgtc gcagtcgcag cggagcatct    540
cgtcgctcta cgaggagcgg ggccacgacc agctgcgcgt gttcgactac gacgagctcc    600
agggcgccac ggccgagttc ggccgcgcgc agaagctcgg cgagggcggc ttcggcagcg    660
tctacaaggg cttcatccgc gccgccgacg gcaaggggga ccgcgtcccc gtcgccgtca    720
agaagctcaa ccagcgtggc atgcaggtcc gtgtccgtcc gtacgtgtgt gtgctcttgt    780
ttgtcctcac tccctccctc cctcctcctg ttgctgtctc tctggttggc ctatctgcga    840
gggcgttcac atgccatcgg tgactcggtt ctccactaca gcctgccatc ggtctctcag    900
tatactacta ccttttttcg gatgacttgg acagatcaga gaagtgggtt ccgggggaat    960
tagtagaatg ggacagatct ctaccgtatt ttccgacaac caggggggt gttcctttat    1020 gttccttttt atgctgtttc actggaacaa tagcatagca ttgataaaac gataaaacac    1080
gtggaactcg cagtttcttt tttcctgctc tcaatctttt ttatctgcat aagcaatgtg    1140
tagtcttgcc agatcagacc aagatgttga atcactgaat gaatcagatg gagtaatcac    1200
agagagtgac atttaggatg cttgcttcga cttcttcaga tctagacaat cttggaagga    1260
aacgaaatag aagggtagt gaagaatttt caaggatccg atgtaggcat tgattagtac    1320
accttatgct gcttttgcag ttggaccatt agtagacgtt aagaccaact aacattttt    1380 ttagtgcgaa aggattccca gtgaaagcat atgtagagtt tatgagccca tcagtgggga    1440
ttggtaaatt tcataacaat gtcagtccat ttctgctgac atttgtaatt gttcgttgc    1500 gaataatcaa tcgctgatta gctgtcagcc ttgtgtagtt ctgtatgtga tatttacagg    1560
caatggaaaa aacatgttat tggagttatg tgcctttgtt caaaaaatat gctaattgga    1620
gggtaagtat agaaataacc atttgattag ctgtaatcta ctgactatag agaaaaaagc    1680
tttagggcat gtttggttca ctacctaagt tgccacactt tgcctaactt ttctgcctaa    1740
ggttagttat tcaatttgga cgactaacct taggcaaagt gtggcacatt tagccacaaa    1800
ccaaacaggc ccttactttg acaaacctga agtaccgggc aaccctcgt ggtttcctcg    1860 aaaaaaggc agtcatgcag aaaagagctg gcagtaagcg caaaaatcat ggatgacctt    1920
ttacatgttc aagaggagaa atatgatatc caggaaagga aacgatgtca accaatcttc    1980
tagctgtatt aaaaaaacca ctactgaatt tgctcgacca atggagacca ctggatagaa    2040
tggacctctt tggtgggcaa taccaacctt agctgactac ttcttactaa gagaccaaat    2100
cttggtatgc caatctgcaa agaaaagtca gctatcattt tgtacaatac attttatcca    2160
tggtttacaa ttgtgaatga tgagctcctg gttttctgaa atgttgactg ataaatagta    2220
aaatatacca ggtatgtgcg gtattgattt ggggtcaaaa gcgaatttgt tttgttgctt    2280
ccttccactg cgcatcggga tgttttcag taataaaaaaa gtgtattctt ggatttatac    2340 agtcacagtga tttaagtgat gatgccgttt taggtgctaa agatatatgt ttttttttca    2400
tcaggaagct gattccacct gtgttagttc caattcgatg cctcgtgcta tctatattat    2460
```

```
ctccctgcac taattgacat atcagaatgt aaattagcta tccttgtctg gaagaaatgt    2520
gctcaaatac aatattaatt agaagtgctt aatgccatag tccaagtgtt cctagactat    2580
caggaaaact gcgttcccta cctgtttcct tatttcttca ttattactgt gacagggaca    2640
taagcaatgg ctggcagaag tacagttcct tggtgttctg gagcacccaa atcttgtaaa    2700
gctacttgga tattgtgctg ttgatagcga aagaggggca cagagattgt tggtctacga    2760
gtttatgccc aataagagct tggaagacca cttgttcagg cgagctaatc ctcctctacc    2820
gtggaacaga aggcttcagg ttatcttggg agctgcagaa ggattggcgt acctgcatga    2880
aggggaagtt caggtaatca ggtgttcttc aagcctgcac tattggtcct gtgctttcaa    2940
tttaccgcca aaggatagcc tatcttccat ggttttttt aaatgggaaa gcatcctagc     3000
tagcaaaagt catcctgact actcgccgca aagattccag gaagctaact tctttgacgt    3060
ttccggaaag cacagctcaa tgttcaaggc taggacatgc aggcgccgta gccaatttca    3120
attgtagctg tgctgtctgt gccaaacatt tcagcctgcc tagcaccggt tctccagctg    3180
actattgtgc gcagcatatg agagccgtca agcaagatca aaatatcaca tattacttgt    3240
gttaagacta cgccatgcca ttgtttcaga acgtgtgcta cagcgctgtt cttgtttgtt    3300
ttcaagtttt tcgttcagaa aagctagacc ttaattttct gcattttggt taggtgatct    3360
accgggactt caaaacgtcc aacattttac tggacaagga cttcagagca aagctatcag    3420
acttcggcct agccagggag gggccaactg gagcaaacac tcacgtctcg actgcggtac    3480
gtacgttaca tccatcaata cgtaggcaat gcagtgtacc tgctcgatct acgcgtagct    3540
gacgaacgac gagcctgggc ttccattgtc aatggtgcat tcactttctt tctatgcgag    3600
catgcacggc actgtcatgt gactgaactg aactattgca ctacgtgcca tgctaacgca    3660
gggcttgaag atagcatcaa gcagtcaatg tgacgcaggg tcgcgctacg gttttgacag    3720
ctctgtggca tgatgtattt tcaggtcgtc gggacgcaag ggtacgccgc accggagtac    3780
atggacacgg ggcacctgac gacgaagagc gacgtgtgga gcttcggtgt ggtgctttac    3840
gagatcctga cggggcggcg gtcgctggac cggaacaggc cggcggcgga gcagaagctg    3900
ctggagtggg tggcccagtt cccgccggac agccgcaact tcggatgat catgaccccc      3960
aggctccgcg gcgagtactc ggtgaaggcc gcccgggaga tcgccaagct ggccgacagc    4020
tgcctgctca agaacgccaa ggagcgcccc accatgagcg aggtggtcga ggtcctcggc    4080
cgggccgtgc aggcgcacgc cgagcctgac agcggggctc ccggcccgg cgccaagggg      4140
aagaagaccg acgctgccac accgtcccgg cggcggcgtg actgactgct acatgtcgtc    4200
atcggtaaag gcgcttaccg agtccattgg ttagtctagt cgtgagctgt gacagcacaa    4260
aaggagtgag tgttgtgctt ggggccctac atataatttt ttttggacat acagcattac    4320
ttagacgtac gtagagacga gctggcggat tgaactttgt gtagctttcg aaagtgagca    4380
ttttgaaaag aaaaaaaaga gtagaggtct caagggtttc gaaagggggc atttcaaaag    4440
attttgcgct ggctctacaa aaggatctgt tttagcatag ccgagtgaaa tcagagtgtc    4500
agacgcgagc gcacagattt tcaggaagc agctggcaag agcttcgtca agcatgtatt      4560
aacagaaaac ataatttata aaaaaaaaat agcgcacaaa tttgattgta                4610
```

<210> SEQ ID NO 5
<211> LENGTH: 6286
<212> TYPE: DNA
<213> ORGANISM: Zea mays

<400> SEQUENCE: 5

```
taaggaacaa ttggatctat accattaaaa gatccaaact ttagatatat accatggacc      60
ccacatgtca ttgactcatg tggacccaca tgtaagtgag atagtaatga tatgatccaa     120
aagtggtgat cttttaatgg tatgatccaa atttccctaa aaataaataa acaaagcgcg     180
cacctactaa tcaaaacgca acagcgcact cgccccctc gcttaaaagc tgtagctcac      240
acgagccgtg ccactgcgag ggaaggaggg agagaaaaag gggagcccga tccaatccca     300
atcccctccc gccgcgtcac atcgccgccg tcctcgtgcc ccgttacctc taaaaccta     360
gcggggagcc gccgagccgg ggatgaagat ccagtgcaac gcgtgcgggg ccgcggaggc     420
gcgggtgctg tgctgcgcgg acgaggccgc gctctgcgtc gcctgcgacg aggaggtgca     480
cgccgccaac aagctcgccg ggaagcacca gcgggtgccg ctcctgacgg acgccgccgc     540
cgctgccgcc gcagcggcgc cggccgtgcc caagtgcgac atctgtcagg tcaggcaccc     600
aggccccgag gcccgagccc tcgtctccgc tgcctctccc tccattcctg tagctcgatt     660
gggttggtgg tgagttggag ttgtcgtgcg gtagctgcca ctgccaggct gggaattttc     720
tactaaccgt ctgatcccaa gctaccaggg tagtctcgcc taatgatttg gctcgcgaag     780
tgaataggcg gctgaagcaa agctgttgtt gatgcttcga tctgtagcaa actgccttgc     840
cttaccttac ctgggcagct tcccttggga tgccgagtct gtttctggag cgttggcgga     900
attgctatac gatatacact atgttttact gatgatctga ctggaccagg acagcagtga     960
gttcaatttt agctcctaca ggctttccct atcccgggga aggcatcatg atgtgatctg    1020
tggctggtcc tgcaggatat tgtaattatg aagaaaccga ctcggatgtt gtactgatgt    1080
gccactcttg aggacccaaa gcaccatttg tcgaccctat ttcttcggga aaaacaaaac    1140
aaaacaaagt gacccatgat tgttacacta aggcctcctt tgggagcaag gataccgaag    1200
gggattagag ggactaaatt cccctccaat ccattccggt attgttgctc ccaaactagt    1260
cctaaggggt gtttggtttc taggtactat ttttagtctt tcaattttat tccattttag    1320
tcctatttaa caattttaaa actaaaatgc aataaaataa agggactaaa aattagtccc    1380
taggaaccaa acatcccta agcattgcat taagactagt actgctgctc tgaacattta    1440
tctctaaaaa gtgctatgtg tttttctgca gtgctgatca ttagtagcta ggttttgctg    1500
agattgttga attgtggtga tatggctatg cttatgttgc ttgtagctgg tgtggtgcag    1560
aagcagggt gaaggggctt atgaggtgtt tggtttctga ggactaattt ttcgtctctt    1620
cattttagtt cctaaattgt caaacacagg gactaaaaga gggattatct ctattttagt    1680
ccatgtgttt ggcagtttac caactaaaag ggactaaaat ggtgggacta aaaattagtc    1740
catagaaact aaacacccc ttacacaatt gatctagagt tggtctatgt ttctccctgt    1800
agccaatggg gtttaagctc aggcttctct taatctgaca ttggaagatg taaattgttg    1860
attgagagag tattgcaaat tatttcttgg ctgggacatt tgtacatact agttagttag    1920
ttaggacgtg tttggtttct agggactaat tttattccat tttagtccct aaattgccaa    1980
atatggaaac taaatctagt ttccatattt tggcaattta gggactaaaa tggagggact    2040
aagtccctgt tcggttcctt tagggggtgt ttggttagag ggactcaaga ttagtctcta    2100
gttttagtc ccattagtc cttttttttg ccaaacacta ggactaaaat atggactaaa    2160
atgacttagt cttagtcct tcacataggt gctaaaagag actaaaagcc cacatgagtg    2220
tattccaaga gcatttgagt cttggacaa tatatttaat gacttagaa tctatttagt    2280
ccctataacc aaacgagtag ggactaaagt ttagtcctag gactaaagct tagtcctaag    2340
```

```
ggggtgtttg gtttctaggg actaatgttt agtcccttca tttaattcct ttttagtata    2400
taaattgcta aatatagaaa ataaaataaa gttttagttt ctatatttgg caattttaga    2460
actaaaatgg aataaaatgt agggactaaa cattagtccc tataaaccaa acacccettt    2520 agtcactaga ctttagtgac taaagtttag tcgctaaagt accccgtttg gttccagtga    2580
ctaaaccgga ctaaagagca ttaattgctg tgaataatga cttttttaccc ctattaatta   2640 atgaatgttt gctataagaa gaaagtggag aggacaaata aggtaaaaat actaatttag    2700 tccctttttag tcacctcctt agtgactaaa gaactaaagt ttagtcaccc cactttagtc   2760
accatgtttg cttctttaga gactaaaatt ggctaaactt tagtcactaa actttagtca    2820
ccccaaacca aatggggcct aaaattagtt catagaaacc aaacaccacc cccttagcta    2880
gccagatgta gtagaaattt ctataaatag aaaagtattg aaaagcatca ataattgcga    2940
ggagaataat taatgttggc tagagttgat catgctgtcc tgcgtggacc caggtatgag    3000
catgcttgct tcaccatact gcctggacta ctaaccatgt gcatgcacat gcagtctcag    3060
tttgcatttc catccttgtt ttgatgaaac ggataagcat tcaatcttga ttcctgatga    3120
agtgtgcaca gaatggccca agccttgatg gtagctttgt tagactacat tgcaattttt    3180
acttgaatga catgtatgtt taaggacaaa tggtgaagat cattctaaat gcatgcatat    3240
agaagctttc tcttcatttg gtcatatatt cttcaaggcc tgaaatatta gagagttaca    3300
tagctaaatg tactacatgc cacgtgaaat ggtacattta actagagtgc accccaatag    3360
gctttacatt gcacttgcgc aagttttctc cttttcacca gcacctaatt taccacaggt    3420
ggaacaaata ggtaatcttc aagatgaaag acaagatcgc tacacaatgg acaatgcaca    3480
caatagctca agctcatgtg tgcgttgcat cccacagtct catgcacatg tttacttaca    3540
gaagttcatg aaaagacacg tgcacttgta agttttaacc accttgaaga agctaaagta    3600
aaacaacatg tgttttctct aattacaaca cattatgtcc tatcattttt tgtaaccttc    3660
acattttctg atttttaaaa cctggtaaat gcgtcaacca tcaaactgta aatttactaa    3720
tcccagtcca tgtatagtga tgccattatt ttgtgtcaac ctaagttatg agtactgtga    3780
acagataaat ttatttgcct ggtgtgtttc tgcaagttgc atttgttttg cttctggttg    3840
ctagatgaaa acccttgttt ctgcactaag ggctgctgta gtgctgttgg gtaggtgtac    3900
cttctgttac tctacattgt tgtacttatg aaggtcgaat cactgtctgg atgatgagtg    3960
aactacattt tacatttttt agtttgttga gttatattgt ccgtggacaa gctgtatctg    4020
gatgtggcca accggcttca ggggctcatg cggctggcac aaggagcaaa caagcaacaa    4080
ccttatcctg agttgctatc attatttgtt agttagctac tagatccatt tggtagtatt    4140
ttatcatctt gctgctagta tgtggttaga gagggcatgt gatcattagt tggaacttgg    4200
cagactagaa gaatatcaat caatattatc ctagtcccat tctcttaccc ttacccttgt    4260
ggtgtggttg ccggctatca gcgaggtcat gctgctgagg ttcagggcca tctagatcag    4320
agtttatcac aacgatatag ttcgctactg cgacacagtt tgttttgtag tgtatcgaat    4380
cctcctgcga gacacttctc atgtttatcc ttactgcagg aggcttctgg atacttcttc    4440
tgcctagagg accgtgcact actttgtaga gactgtgatg ttgctataca cacagtgaat    4500
tcctttgttt cagtacatca gagattcctg ctaactggag ttcaggtggg tcttgatcct    4560
gctgatccag ttccacctat tgctgaaaag catgttaatg ctgttggtgg atcagtgaat    4620
caaccagtga gacatcagcc aaggagaagc ccgacagttc aattttcagt tgaagggagt    4680
gcttctgttc ctaccaaaaa tgtaacaaat ggagattgtt caaggcagaa ttttgtccca    4740
```

-continued

```
acagccaggg cagaagtggt tgattggact atgaataata gtacaattcg atcagtagaa    4800
tctccgccta agtacatttc agaggaaagc cccacacttc tgcaatctag ccagaccaca    4860
acagtcttct ccaaccaaat taatggcaat agtgatgggg cctaccactt gtcattctca    4920
ggtggtaatg tgacagacag cctaccagat tgggcccgtgg atgagttctt cagtaactca   4980
gaatatggtc caaactttgg cttctccgag aatggttctt ctaaggcaag ttactatata    5040 tacattttt ttctttatct ttttgcctct ctttcctcca tatcgttaat agcctactag     5100
cttctgttca gttttatggt cttttagact gctgattcac ataggcagca tttcttgatg    5160
cggatgttca tgttatttct tgcatagttc atggttgact agcttcatgc atttgaactt    5220
gtgaactttt actatgacga aaattcagat tgttgttgta aacatgattt aagagcttga    5280
gagtgacatc ctttctggca tctacatgaa gaaagttaat tgataaggtt atttaggttg    5340
aaaattgatc ggatccgttg ttaactggct gatggtgaac tagagtttca gatctgtgct    5400
gttgtagtgc taggtttagt tgctacattt ggtgaccgtt actctagttt aggagattgc    5460
tctttgcagt agtccaggct ttgtggattg tgacatgatg acgatcaaca tttggtttta    5520
gcgtagcatc aaatttgtgc attcacttga aatacttaaa atacaaactg ctgaataccg    5580
tttctctttt tacagggtga taccgctaag ctgggggggcg ctggtggatc tccacaatgc   5640
cgtttggctg aaggctcagt tgctgaggaa ctattagggc aggtgcctgg attgatcacc    5700
gatgaatata tgggccgagt acctgagaat tcatggacag tgcctgaggt tccctctcca    5760
ccaacagcct cggggctcaa ctggcatggg aatttgtgtt tccctgcgta tgacagcacc    5820
atgtttgttc ctgaaattac ctccctccag aactcccaaa gtcacttcac cgtaccttcc    5880
agtttcaagc gccggagaag agagtactaa gaggcgacaa gaagatcact agacaccact    5940
gtccggtcta ggccatcttg agaaaggctt cttggtgggc caaatgacga aagaaaatat    6000
ccaggactga gtggtcattc aaacatcaac tgagctatcc agtagccagg ttttaagtgt    6060
gttgtaatgc ttcaatgtgt ttcattttct aaagacctga gcttcgcttg tgatttgttc    6120
cgagctgtac ggtgtcgatt ttgtgtatat aatataatat accgaaataa agggtaccca    6180
ttatgagtat atgatcattc cgaaataaag ggtatcccgt atgagtatga tcattcgcga    6240
gtacatcgca cactggtggt ggcacattaa gttacttctg caatac                 6286
```

<210> SEQ ID NO 6
<211> LENGTH: 11
<212> TYPE: DNA
<213> ORGANISM: Zea mays
<220> FEATURE:
<221> NAME/KEY: misc_feature
<222> LOCATION: (7)..(7)
<223> OTHER INFORMATION: Chr3, SNP designation 17606436

<400> SEQUENCE: 6

```
tagcagygtc g                                                          11
```

<210> SEQ ID NO 7
<211> LENGTH: 14
<212> TYPE: DNA
<213> ORGANISM: Zea mays
<220> FEATURE:
<221> NAME/KEY: misc_feature
<222> LOCATION: (8)..(8)
<223> OTHER INFORMATION: Chr3, SNP designation 17606457
<220> FEATURE:
<221> NAME/KEY: modified_base
<222> LOCATION: (9)..(11)

```
<223> OTHER INFORMATION: This region may or may not be present in its
      entirety

<400> SEQUENCE: 7
gccgccatgc ggcg                                                      14

<210> SEQ ID NO 8
<211> LENGTH: 11
<212> TYPE: DNA
<213> ORGANISM: Zea mays
<220> FEATURE:
<221> NAME/KEY: misc_feature
<222> LOCATION: (9)..(9)
<223> OTHER INFORMATION: Chr4, SNP designation 4808588

<400> SEQUENCE: 8
ggtgtactya t                                                         11

<210> SEQ ID NO 9
<211> LENGTH: 11
<212> TYPE: DNA
<213> ORGANISM: Zea mays
<220> FEATURE:
<221> NAME/KEY: misc_feature
<222> LOCATION: (7)..(7)
<223> OTHER INFORMATION: Chr4, SNP designation 4808626

<400> SEQUENCE: 9
gttctcrgtt t                                                         11

<210> SEQ ID NO 10
<211> LENGTH: 11
<212> TYPE: DNA
<213> ORGANISM: Zea mays
<220> FEATURE:
<221> NAME/KEY: misc_feature
<222> LOCATION: (2)..(2)
<223> OTHER INFORMATION: Chr7, SNP designation 126746831

<400> SEQUENCE: 10
ckgaagacta c                                                         11

<210> SEQ ID NO 11
<211> LENGTH: 13
<212> TYPE: DNA
<213> ORGANISM: Zea mays
<220> FEATURE:
<221> NAME/KEY: misc_feature
<222> LOCATION: (10)..(10)
<223> OTHER INFORMATION: Chr7, SNP designation 143394449
<220> FEATURE:
<221> NAME/KEY: modified_base
<222> LOCATION: (11)..(12)
<223> OTHER INFORMATION: This region may or may not be present in its
      entirety

<400> SEQUENCE: 11
tcgcatagaa taa                                                       13

<210> SEQ ID NO 12
<211> LENGTH: 17
<212> TYPE: DNA
<213> ORGANISM: Zea mays
<220> FEATURE:
<221> NAME/KEY: misc_feature
<222> LOCATION: (7)..(7)
<223> OTHER INFORMATION: Chr9, SNP designation 19033476
<220> FEATURE:
<221> NAME/KEY: modified_base
```

```
<222> LOCATION: (8)..(13)
<223> OTHER INFORMATION: This region may or may not be present in its
      entirety

<400> SEQUENCE: 12
acagctttgc agttgct                                                    17
```

METHODS AND PRODUCTS FOR CONTROLLING SILK FLY AND PHORID FLY IN MAIZE

CROSS REFERENCE TO RELATED APPLICATIONS

This application is a Continuation of U.S. patent application Ser. No. 16/096,667, filed under 35 U.S.C. § 371 on Oct. 25, 2018, which claims priority to International Application No. PCT/US2017/064711, filed on Dec. 5, 2017, which applications are incorporated herein by reference in their entirety.

SEQUENCE LISTING

The instant application contains a Sequence Listing which was submitted electronically in ASCII format in the parent application (U.S. patent application Ser. No. 16/096,667). The original Sequence Listing was created on Nov. 30, 2017, and was named 101008132_100WO1_SL.txt and was 21,878 bytes in size. The identical Sequence Listing is resubmitted herewith as of Feb. 1, 2021, and named 101008132_100US3_SL.txt and is 21,878 bytes in size.

FIELD OF THE INVENTION

The present invention is directed to novel methods for producing maize plants, plant materials and seeds that provide a means of controlling and defending against the corn silk fly and phorid fly and improved maize plants, plant materials and seed produced by these methods. The unique methods utilize molecular markers to incorporate genes to provide a means of controlling and defending against the corn silk fly and the phorid fly into the male and/or female parent lines of maize hybrid plants, plant parts and seeds, or into at least one of the maize parent lines of a hybrid. The unique methods also provide a means for testing and identifying the presence of the genes which are responsible for controlling and defending against the corn silk fly and phorid fly in maize plants.

BACKGROUND OF THE INVENTION

Maize Crops and Insect Pests

Corn (maize) is one of the world's oldest and most widely grown crops. Human beings have cultivated and used it for centuries. Maize plants have ten chromosomes, and the maize genome was originally very diverse, consisting of a number of different types of corn, which are generally classified by characteristics of their kernel endosperm. The most common types of corn include flint (*Zea mays* var. *indurate*), flour (*Zea mays* var. *amylacea*), dent (*Zea mays* var. *indentata*), pop (*Zea mays* var. *everta*), sweet (*Zea mays* convar. *saccharata* var. *rugosa*), waxy (*Zea mays* var. *ceratina*) and pod (*Zea mays* var *tunicata*). The physical appearance of the plants of each type varies, as do their kernels and other characteristics.

Over time, as maize became increasingly domesticated by human beings, much of its original genetic diversity was either lost or became increasingly difficult to access by plant breeders. ("Genetic Vulnerability of Major Crops," Natl. Acad. Sci., Washington, D.C., ISBN 0-309-02030-1, Library of Congress Catalog Card Number 72-77533, 100-01 (1972)). Moreover, maize selection processes based upon genotype and/or phenotype, and structured plant breeding programs developed by research institutes, universities, and private and public companies, have modified the original diverse maize genome, resulting in diminished maize crop diversity and, thus, more genetically restricted maize species diversity. This reduction in maize crop diversity has resulted in a number of maize plant species now being grown in large homogeneous stands, which has resulted in an increased likelihood of insect pest infestations to the maize crops. Insect pests are responsible for substantial maize crop losses worldwide. Insect infestations adversely affecting maize crops have, in the past, been addressed by breeders and growers largely via applications thereon of chemical pesticides and/or insecticides manufactured and/or distributed by a number of different companies. Insect infestation in maize crops has also been addressed using molecularly engineered or transgenic products commonly referred to as "GMOs" (Genetically Modified Organisms).

It has been well documented that significant economic losses have been suffered due to insect pests that can markedly reduce the amounts of agricultural produce, such as maize crops. These economic losses have adversely impacted all different types of maize crops, but are especially acute in maize crops such as sweet corn, a substantial portion of which is typically eaten by human beings as a vegetable.

Sweet corn is a type of maize plant that is classified as *Zea mays* convar. *saccharata* var. *rugosa*, and has white, yellow, bi-colored or multi-colored kernels that typically have a high sugar content. Sweet corn is typically eaten by human beings as a vegetable, either directly from the maize cob, or by having the sweet kernels removed from the cob, and may also be either canned or frozen, and is a major vegetable crop that is grown all over the world primarily for fresh consumption. The fruit of the sweet corn plant is the corn kernel, and the ear consists of a collection of kernels on the cob. The ear is covered by tightly wrapped leaves (the husk).

Because sweet corn is most often eaten fresh on the cob, the physical appearance of its kernels, its cob and its husk surrounding the cob is very important to consumers worldwide. Husks, kernels and cobs that show insect infestation and/or damage are typically not desired by consumers, and are often rejected by retail purchasers and consumers at the point of sale (i.e., plant stand, supermarket, grocery store, or the like), thereby leading to substantial wasted product, spoilage and resulting economic losses. To be desirable to consumers, maize husks need to appear unblemished, with few or no holes or other damage, caused by insects. The kernels on the maize ears must generally also be smooth, plump and unwrinkled to be desired and purchased by retail buyers and consumers. Evidence of insect damage to maize husks, kernels and/or cobs often leads to unmarketable product and resulting economic loss.

Corn Silk Flies

Corn silk flies are destructive, metallic green to black colored flies having distinctive wing patterns, and wing flapping behavior and a preference for sweet corn ears. They are increasingly becoming a major insect pest in significant sweet corn production areas worldwide, and sweet corn consumers have virtually no tolerance for corn silk fly damage. In the past 50 years, the sweet corn industry has grown dramatically worldwide and, thus, the corn silk fly has become increasingly more important. Numerous species of this insect pest exist primarily in tropical and subtropical areas of the western hemisphere. Corn silk flies can be found throughout Florida, Puerto Rica, the Caribbean Islands, Mexico and Central and South America to Argentina and Chile, and are also prevalent in other parts of the world. Sweet corn and other maize types are the most susceptible to damage by the corn silk fly during the first few days after its silk emergence, and prior to silk senescence. Entire fields of sweet corn can be destroyed, and not considered for harvest by breeders and/or growers, if they go untreated for these destructive pests, or if individual treatments are missed due to weather, time or other constraints. Similarly, maize ears produced for seed and silage are also vulnerable to attack by these insects, which can result in significant yield reductions or with product being destroyed. A present continuous and growing market demand for fresh sweet corn has required a use of sequential planting of sweet corn crops that moves northward from the southern tip of Florida into Georgia, thereby facilitating the movement, and spread, of the corn silk fly into new and more temperate production regions, aiding its adaption to cooler weather patterns, and increasing a need for specific insect control strategies and host plant resistance. (B. T. Scully et al., "Resistance in Maize to *Euxesta stigmatias* Loew (Diptera: Otitidae)," J. Entomol. Sci. 35(4): 432-443 (2000)).

Numerous species of corn silk flies are prevalent in Florida, including *Chaetopsis massyla, Euxesta annonae, Euxesta eluta, Euxesta stigmatias* and others. The genus *Euxesta* is represented by 36 corn silk fly species in North America (north of Mexico), and 69 such species in the Americas south of the United States (central and South America). The genus *Chaetopsis* is represented by seven corn silk fly species in North America, and ten such species in the Americas south of the United States, with four such species common to both. An even more damaging corn silk fly known as the phorid silk fly has been identified in southern Florida.

The corn silk fly can inflict immense damage on sweet corn. Such damage can result in "poor kernel set," thereby undesirably producing asymmetric kernel size and/or rows on the cob. Further, adult females typically lay clusters (generally 8 to 40) of their white oblong eggs, generally about 1.0 mm long, on corn silk emerging from sweet corn husks, and underneath the husks protecting the silk channel. (B. T. Scully et al., "A Rating Scale to Assess Damage Caused by the 'Corn Silk Fly' (*Euxesta stigmatias* Loew) (Diptera: Otitidae) on the Ears of Sweet Corn," Subtropical Plant Sci. 54:34-38 (2002)). Corn silk fly larvae subsequently hatch (usually in two to four days) and resulting ear-feeding maggots typically begin feeding on, and down, the corn silk, ultimately penetrating the corn kernel pericarp and feeding on developing kernel endosperm. Up to several hundred maggots can feed on a single sweet corn (or other maize) ear, and the larval stage commonly lasts about 20 days, after which the larvae typically exit the sweet corn ears, jump off of the plants, and pupate the soil (Scully et al. 2002). Adults generally emerge in about five to nine days, and the life cycle of the corn silk fly is usually completed in less than three weeks, with reproductive adults possibly living up to four weeks (Scully et al. 2000). Large numbers of corn silk fly larvae generally result in wet, decomposing corn silk within the silk channel of the corn ears, thereby making such ears unmarketable without first trimming the ears to remove their tips. Such trimming undesirably results in a poor ear appearance and diminishes ear size. Corn silk fly larvae also feed on the tips of the cobs, resulting in "blank tips." Larvae that feed down into the ears typically cut into the pericarps of developing corn kernels, and often hollow out their interiors (endosperm), thereby destroying them. Corn silk larvae may also be disadvantageously found feeding along the entire length of corn ears, and resulting extreme damage thereto can very undesirably result in twisted, unsightly ears with few, if any, kernels.

Phorid Flies

Phorid flies (Diptera) are similarly very destructive insects that damage the silk tissue, the tips of the cob, and have been observed to disrupt pollination, leaving the top of the cob 25-50% bare of kernels at harvest. (David Owens et al., "Cob Flies, *Megaselia* spp. (Diptera: Phoridae), in Sweet Corn," Univ of Fla Entomol & Nematol 5 (2016).) Like the corn silk fly, the phorid fly is increasingly becoming a major insect pest in significant sweet corn production areas worldwide and sweet corn consumers have virtually no tolerance for phorid fly damage. Phorid flies have a very distinct appearance and behavior. Adult phorid flies are 2-3 mm in length, about half the length of silk flies (4-7 mm). (Owens et al. 2016 at 3.) Adult phorid flies are light brown with dark brown to black markings on the dorsal side of the abdomen. Their hind femurs have a dark pigmentation at the end. They have no dark bands across their wings, further distinguishing themselves from silk flies. The wings of phorid flies have heavy veins that curve to meet the wing margin about half way between the wing tip and the body. The head of the phorid fly is small and has large, black bristles. Phorid flies have a very distinctive locomotion. They move very quickly in a "herky-jerky" fashion characterized by short, rapid running, a pause, a turn, and more short, rapid running. For this reason, they are known as humpback flies or scuttle flies. (Owens et al. 2016 at 1.) Phorid flies are also sometimes called "cob flies" because of the damage that they inflict on the cobs of maize plants.

Phorid flies are part of the genus *Megaselia*, which is very diverse, with more than 1400 described species. (Owens et al. 2016 at 1.) The species (*Megaselia seticauda* Malloch) has been observed to damage maize. *Megaselia seticauda* was first observed in Costa Rica in 1914. (Owens et al. 2016 at 1.) There were later reports of damage by phorid flies to immature "green corn" ears in Texas (1944), Mexico (1942) and Ecuador (1954). Phorid flies were observed in Brazil (1962) and detected in California (1996). (Owens et al. 2016 at 1.) By 1950, in Texas, fields that were not treated with DDT for corn earworm were severely infested with both *M. seticauda* and the silk fly *Euxesta stigmatias* (Diptera: Ulidiidae). Larvae of both *E. stigmatias* and *M. seticauda* were reported as being relatively unaffected by DDT spray residues, leading to the recommendation to treat adults. (Owens et al. 2016 at 1.)

Phorid flies have increasingly become a major insect pest in Florida where crops are being grown for organic and other specialty markets, without the protection of insecticides. Phorid flies have been found in both sweet corn and field corn in Florida where insecticides have not been applied. (Owens et al. 2016 at 1.) In April 2016, ears of early-silking sweet corn in a variety trial where an organophosphate insecticide had been applied at the UF/IFAS Everglades Research and Education Center in Belle Glade, Fla., were found to be heavily damaged by phorid larvae. (Owens et al. 2016 at 1.) The phorid larvae were observed to develop faster and cause damage quicker than silk fly.

Phorid fly larvae are distinguishable from larvae of silk flies by the tapering shape of the posterior abdomen. (Owen et al. 2016 at 2.) In contrast, silk fly larval abdomens terminate bluntly, and two dark-colored, peg-like spiracular (breathing tube opening) plates can be easily seen at the end of the abdomen. Phorid flies retain their white coloration throughout the larval stage. When the larvae emerge from the eggs, they enter the ear to feed on silks, cob and kernels. Once they reach the ear, larvae feed on the cob and developing kernels at the tip. Phorid flies leave the ear 10-14 days after first silk, usually before blister stage, by leaving a visible shiny mucous trail on the drying silks. Damaged silk tissue is reddish brown to brown. (Owens et al. 2016 at 4.) Heavily damaged silk appears wet and slimy. Severe tip damage can occur on ears that are still at least one week to ten days from harvest. Because larvae develop faster and leave the ear earlier than silk fly, phorid flies may be partly responsible for the damage often attributed to silk fly.

Growers experiencing insect pressure from the phorid fly have traditionally used insecticides as a means of control. Insecticides such as DDT are no longer acceptable to be applied to crops in many growing regions around the world. Other less toxic insecticides sometimes require multiple applications to control these insects.

Agricultural Pesticides and Insecticides

In the 20th century, benefits for agricultural crops appeared to be produced using agricultural chemical pesticides and/or insecticides to control agricultural insect pests. A large crop protection industry developed around chemical pesticides and insecticides during the mid to late 20th century. Increasingly, however, and disadvantageously, chemical pesticides and insecticides came to be viewed by scientists as a potential threat to both living organisms and the environment. Pesticides and insecticides are presently heavily tested, and regulated by governmental regulatory agencies before they can be registered for application. In several instances, previously-approved pesticides and/or insecticides have been reported by researchers to pose a potential risk to the health of humans, animals and other forms of life, including a potential risk of cancer.

Most clinicians and researchers hold the opinion that no segment of the population is completely protected against exposure to pesticide and/or insecticide use, and the potentially serious detrimental health effects thereof. (See W. Aktar et al., "Impact of pesticides use in agriculture: their benefits and hazards," Interdiscip Toxicol. 2(1):1-12 (2009).) Higher risk population groups include agricultural farm workers, production workers, formulators, sprayers, and loaders. Certain pesticide and/or insecticide compounds and residues, known as "organochlorine compounds," have a potential to pollute the tissues of life forms on land (human beings and animals), in the air (birds, bats and the like) and in lakes and the oceans (fish, seals, whales, other sea mammals and other marine life forms). Certain other pesticide and/or insecticide compounds, known as "endocrine disruptors," have been reported by researchers to disadvantageously elicit adverse effects by mimicking and/or antagonizing natural hormones that are present in the human body. Research suggests that long-term, low-dose exposure to such pesticides and/or insecticides very disadvantageously can be associated with adverse health effects to human beings and animals, such as immune system suppression, hormone disruption, mental disorders, reproductive abnormalities and/or cancer. In food commodities, pesticide and insecticide use has had a serious and substantial impact. In addition, the use of specific pesticides and insecticide has been reported to result in contamination of soil, water, turf and other forms of vegetation.

Applying pesticides and insecticides to growing crops is expensive, and often must be repeated, sometimes weekly, to achieve effective control of the targeted insect. Due to physical and time constraints that are often associated with treating large areas of maize plants with ground machinery, such chemicals are sometimes applied aerially, which is also expensive, potentially wasteful of the chemicals, and potentially dangerous for the pilots (Scully et al. 2000).

Genetic Engineering of Insect Resistance Traits into Agricultural Plants

In the 20th century, due in part to adverse health concerns associated with chemical pesticides and insecticides, agricultural plants, including maize, had been modified using genetic engineering technology to incorporate a new trait of insect resistance into the agricultural plants themselves.

To accomplish the above, one or more genes from outside of the maize (or other plant) genome were artificially introduced into maize transgenically using a set of several biotechnology techniques that are collectively referred to as "recombinant DNA technology" techniques. DNA spliced to the coding portion of such genes that served to regulate how they functioned were also transferred into the new host plant. The inserted genes, called "transgenes" when they were inserted into the new host plant, may have come from another plant of the same or a different species, or a completely unrelated kind of organism, such as bacteria or an animal. The gene being transferred into the new host may have had its genetic code altered to modify its function, in addition to having different regulatory sequences spliced thereon to control how it was expressed (switched "on" or "off") in the new host plant.

The process of moving genes from one species to another is called "transformation." Once a "transgenic plant" is created, the "transgenes" can be inherited along with the rest of the plant's genes through mating by pollination. The host plant's offspring are also "transgenic" when they acquire the "transgenes" in this manner. As a result of the foregoing, plant breeders could take a "transgenic plant" made in the laboratory and use various breeding techniques to develop different transgenic varieties of the plant that are adapted for specific uses, all with the new plant trait provided by the introduced genes from outside of the plant.

Plants commercialized with the above technology have typically been referred to as GMOs. GMOs are essentially any organism that has undergone a recombinant DNA procedure. Recombinant DNA technology involves the transfer of genetic material from one organism to another plant or animal. The genetic engineering process can be achieved by utilizing viruses and/or bacterial DNA to implant the desired gene(s) into the target host plant or animal. Genetic engineering has been performed in plants for food crops, trees, grasses, flowers, industrial products, pharmaceuticals, and environmental remediation and conservation.

In general, through the use of recombinant DNA technology, agricultural researchers have reported some improvements in forestry and tree-related characteristics associated with insect pest and disease (virus, bacteria and fungi) resistance. Additionally, such researchers have correlated the use of recombinant DNA technology with some increased energy production, increased efficiency of pulp milling, straighter trees for lumber and building and transgenic modifications of tree fruits to improve flavor and color. Genetic engineering in grasses and flowers has reportedly achieved improvements in: herbicide, insect pest, and disease resistance, stress tolerance (enhanced tolerance to heat, cold, and drought), and product characteristics.

In relation to industrial products, genetic engineering is being conducted to produce proteins, biopolymers, plastics, fatty acids, oils, waxes and dyes.

There has been a substantial amount of criticism by consumers regarding the use of genetically modified products in food, however, and many consumers globally are not in favor of GMOs. Critics of genetically modified foods advocate that the risks have not yet been adequately identified and/or managed. Questions have also been raised by consumers as to the objectivity and effectiveness of food product (and other) regulatory authorities. Some organizations advocate that there are too many unanswered questions regarding the potential adverse long-term effects on health due to the ingestion of genetically modified foods, and have proposed mandatory labeling, or even a moratorium on such food products.

Need for Alternative Insect Control and Defense Methods for Maize Crops

The use of chemical pesticides and insecticides, and of GMOs, to protect maize crops from insect pest damage are established practices. However, consumers and retail buyers have expressed serious health and environmental concerns over these traditional means of insect pest control.

There has, therefore, been a long-felt and unfulfilled need for a more wholesome and health-conscious approach to insect pest control, and to the production of food products that do not contain either pesticide or insecticide residue on the one hand, or genes that have been transgenically introduced into the maize genome from sources outside of the maize genome on the other hand. With respect to sweet corn, in particular, and maize generally, there has been a long-felt need in the sweet corn and maize industries for a wholesome and health-conscious method for providing a means for controlling and defending against insect pests, such as the corn silk fly and the phorid fly (all species and types).

Plant breeders have attempted for many years to develop a maize genetic source of insect pest resistance. In 1992, N. W. Widstrom et al., "Recurrent Selection for Resistance to Leaf Feeding by Fall Armyworm on Maize," Crop Sci. 32:1171-1174 (1992), reported indications that the use of "recurrent selection breeding" methodologies (reselection generation after generation, with intermating of selected plants to produce the population for the next cycle of selection) could be useful in developing insect protection utilizing an "exotic maize synthetic" (uncommercialized wild-type accessions collected from around the world). However, while Widstrom expressed hope that "recurrent selection breeding" would accomplish the foregoing goal, time passed, and there are no significant successes reported of increasing control over or defending against insect pests utilizing such conventional plant breeding methodologies.

Because no commercially-available sweet corn cultivars were known to provide control over or defense against the corn silk fly, control practices focused instead on insecticide use, rather than on host plant resistance (Scully et al. 2000; Scully et al. 2002). Very few studies cited maize lines having any inherent resistance at all to the corn silk fly. A study in Brazil reported that two sweet corn test hybrids showed some resistance to an unknown species of *Euxesta*, however, no sweet corn varieties having control over or the ability to defend against *Euxesta* have ever been commercialized in the United States or any other parts of the world. (See M.C. et al., "Avaliacao da Resistencia a *Helicoverpa zea* (Boddie) Lepidoptera: Noctuidea) e *Euxesta* sp. (Diptera: Otitidae) em linhagens de milho-doce," An. Soc. Entomol. Brasil 23(1):136-140 (1994).) No host plant resistance to *E. stigmatias* has ever been identified in sweet corn or maize generally (Scully et al. 2000).

In 2000, agricultural researchers considered whether field corn could provide a source of resistance to corn silk fly for improvement of sweet corn in regard to damage from corn silk flies (Scully et al. 2000). The study concluded that, in order to lower the susceptibility of sweet corn to the corn silk fly, many different factors still needed to be better understood, for example, the role of the endosperm mutant genes, and their pleiotropic effect, on silk biochemistry, and the genetic basis of, and mechanism of resistance to, the corn silk fly in the corn ear. Researchers thereafter continued their efforts to find a source of corn silk fly resistance from the maize genome to effectively control such insect pest.

To date, efforts to achieve corn silk fly protection in maize crops to a commercially-acceptable level have been limited by a number of different factors. Hindrances to maize breeders and growers have included no, or limited, access to insect rearing facilities, negative characteristics associated with donor genetic and other materials, complications from multiple gene factors and gene interactions, epistasis (a certain relationship between genes in which an allele of one gene hides or masks the visible output, or phenotype, of another gene), environmental influences and considerable time requirements. In addition, further complications exist, such as incomplete knowledge and characterization of the actual insect pest protection gene sequences and their specific locations on the respective chromosomes.

Control and Defense of Other Types of Insect Pests in Maize

Agricultural researchers have conducted studies to try to control other types of insect pests, such as Lepidopteran larvae, in maize crops. (Lepidoptera is an order of insects that includes moths and butterflies, both called lepidopterans.) With respect to fall armyworm, *Spodopter frugiperda* (J. E. Smith) (Lepidoptera: Noctuidae), and southwestern corn borer, *Diatraea grandiosella* Dyar (Lepidoptera: Crambidae), QTL regions on chromosomes 1, 5, 7, and 9 in maize inbred line Mp708 and its resistant parent Mp704 have been identified as conferring resistance to both insects. (T. Brooks et al., "Genetic Basis of Resistance to Fall Armyworm (Lepidoptera: Noctuidae) and Southwestern Corn Borer (Lepidoptera: Crambidae) Leaf-Feeding Damage in Maize," J. Econ. Entomol. 100(4):1470-1475 (2007)). However, no studies have reported any correlation between resistance to fall armyworm and southwestern corn borer and corn silk fly and phorid fly resistance.

Furthermore, researchers have identified a 33 kDa cysteine protease (an enzyme that degrades proteins) called "maize insect resistance cysteine protease" (Mir1-CP) as having plant protection attributes. Results of these studies indicated that, in specific maize lines, there is a rather rapid accumulation of Mir1-CP in the whorls of their husk leaves in response to feeding by Lepidopteran larvae. Researchers observed that this naturally-occurring cysteine protease is located in the maize roots and vascular tissues, and is readily mobilized in response to insect herbivory. In vitro studies suggested that Mir1-CP completely permeates the insects' "peritrophic matrix" (PM), an extracellular envelope that lines the digestive tract of most insects, and is composed largely of proteins and glycosaminoglycans embedded in a chitinous matrix, and protects the insects' midgut epithelium from mechanical damage, pathogens and toxins. These studies also suggested that Mir1-CP plays an active role in maize plant digestion and nutrient absorption by digesting (breaking down) PM proteins to retard insect growth. Studies also indicated that Mir1-CP was most effective on Lepidopteran larvae belonging to the Noctuidae family, the largest and most economically important family of Lepidopterans.

Mir1-CP is a papain-like cysteine protease that has amino acid sequences in common with several other baculoviruses that infect Lepidopteran larvae. However, Mir1-CP is the only reported defensive cysteine protease that has shown to directly damage the Lepidopteran PM. U.S. Pat. No. 5,977,440, issued in 1999, describes the cDNA encoding Mir1-CP, and a method of conferring insect resistance on a plant susceptible to Lepidopteran feeding by expression of Mir1-CP in the plant.

Since Mir1-CP was identified, few maize parent lines or hybrids were ever commercialized using the Mir1-CP gene, and no sweet corn parent lines or hybrids containing Mir1-CP were ever commercialized. Instead, the field corn and sweet corn industries continued to use chemical pesticides and insecticides and GMOs as the basic source of insect protection in maize.

Despite the efforts of many agricultural researchers, prior to the present invention, no form of commercially acceptable genetic control has been identified as a means for controlling infestations of the corn silk fly or the phorid fly in maize crops. The present invention, therefore, provides a long felt, but unresolved, need in the maize breeding and growing industries for a more wholesome and health conscious approach to insect pest control in maize plants, and to the production of maize ears and kernels (and other food products) that do not contain pesticide and/or insecticide residue or genes that have been transgenically introduced therein from sources outside of the maize genome.

SUMMARY OF THE INVENTION

The present invention provides unique, cost-effective, reliable and successful methods for breeding, growing, developing and producing maize plants, plant materials and seeds that very advantageously provide a wholesome, natural and health conscious means of controlling and defending against corn silk flies and phorid flies, and to the improved maize plants, plant materials and seeds that are produced by these methods, which have one or multiple desirable characteristics for consumers of these products, as well as for commercial plant growers and home gardeners. The inventive methods do not employ pesticides and/or insecticides, or genes that have been transgenically introduced into maize plants, plant materials or seeds from sources outside of such plants, plant materials or seeds, to control corn silk flies and phorid flies, and the resulting products, thus, do not contain pesticide or insecticide residues, and are not GMOs. In contrast, the inventive methods utilize one or a plurality of molecular markers to assist in incorporating genes to provide a means of controlling and defending against the corn silk fly and phorid fly into the male and/or female maize parent lines of maize hybrid plants, plant materials or seeds (i.e., into at least one of the two maize parent lines of such hybrids). The unique methods also provide a means for testing and identifying the presence of the genes which are responsible for controlling and defending against the corn silk fly and phorid fly in maize plants.

The present invention provides a novel construction of genetic elements that confers a high, or an enhanced, degree of maize plant protection from the corn silk fly (all species and types) onto maize plants, plant materials and seeds, thereby preventing, or reducing, significant or substantial losses in yield and quality of maize plant crops, and their related plant materials and seeds, and a corresponding loss in revenues from sales of maize plants, ears and seed.

In one aspect, the present invention provides a method for producing a hybrid maize plant, plant material or seed having a maize genome-based form of controlling and defending against corn silk flies and phorid flies without the use of chemical pesticides or insecticides.

In another aspect, the present invention provides a hybrid maize plant, plant material or seed that provides control over and defends against corn silk flies and phorid flies in comparison with a conventional hybrid plant, plant material or seed.

In still another aspect, the present invention identifies single nucleotide polymorphisms (SNPs) and indels that may be used in a marker assisted selection process to produce inbred maize parent lines, hybrid maize plants, plant material or seed that provides control over and defends against corn silk flies and phorid flies.

In another aspect, the present invention provides hybrids and inbred lines of maize plants, plant material or seed comprising quantitative trait locus regions that control or defend against corn silk fly and phorid fly.

In another aspect, the present invention provides a method for producing a hybrid maize plant, plant material or seed comprising quantitative trait locus regions that control or defend against corn silk fly and phorid fly, comprising the following steps:
  (a) identifying one or more maize parent lines containing one or more of the SNPs or indels that have been identified as providing control or defense against corn silk fly and phorid fly utilizing molecular markers;
  (b) incorporating one or more of the SNPs or indels that provide control or defense against corn silk fly and phorid fly into a male or female inbred maize parent line;
  (c) crossing the male or female inbred maize parent line containing one or more of the SNPs or indels that provide control or defense against corn silk fly and phorid fly with another inbred maize parent line to produce a hybrid; and
  (d) optionally, conducting one or more genetic identification tests to confirm that the hybrid contains the SNPs or indels that provide control or defense against corn silk fly and phorid fly.

In another aspect, the present invention provides a method for producing a male or female inbred maize parent line that provides control or defense against corn silk fly and phorid fly, comprising the following steps:
  (a) identifying one or more maize lines containing one or more of the SNPs or indels that have been identified as providing control or defense against corn silk fly and phorid fly utilizing molecular markers;
  (b) incorporating one or more of the SNPs or indels that provide control or defense against corn silk fly and phorid fly into a male or female inbred maize parent line;
  (c) utilizing recurrent selection or other plant breeding methods to produce a male or female inbred maize parent line containing one or more of the SNPs or indels that provide control or defense against corn silk fly and phorid fly; and
  (d) optionally, conducting one or more genetic identification tests to confirm that the inbred maize parent line contains the SNPs or indels that provides control or defense against corn silk fly and phorid fly.

In another aspect, the present invention provides a hybrid maize plant, plant material or seed prepared by a process comprising the steps of:
  (a) identifying one or more maize parent lines containing one or more of the SNPs or indels that have been identified as providing control or defense against corn silk fly and phorid fly utilizing molecular markers;
  (b) incorporating one or more of the SNPs or indels that provide control or defense against corn silk fly and phorid fly into a male or female inbred maize parent line;

(c) crossing the male or female inbred maize parent line containing one or more of the SNPs or indels that provide control or defense against corn silk fly and phorid fly with another inbred maize parent line to produce a hybrid; and (d) optionally, conducting one or more genetic identification tests to confirm that the hybrid contains the SNPs or indels that provide control or defense against corn silk fly and phorid fly.

In another aspect, the present invention provides a male or female inbred maize parent line prepared by a process comprising the steps of:

(a) identifying one or more maize lines containing one or more of the SNPs or indels that have been identified as providing control or defense against corn silk fly and phorid fly utilizing molecular markers;

(b) incorporating one or more of the SNPs or indels that provide control or defense against corn silk fly and phorid fly into a male or female inbred maize parent line;

(c) utilizing recurrent selection or other plant breeding methods to produce a male or female inbred maize parent line containing one or more of the SNPs or indels that provide control or defense against corn silk fly and phorid fly; and (d) optionally, conducting one or more genetic identification tests to confirm that the inbred maize parent line contains the SNPs or indels that provide control or defense against corn silk fly and phorid fly.

In another aspect, the present invention provides hybrid and inbred line *Zea mays* or *Zea mays*, convar *saccharata* var. *rugosa* maize plants that are produced by the methods described above. Among the products of the present invention are Sweet Corn Hybrid NBDX 1001 and Sweet Corn Hybrid NBDX 1002 and inbred parent lines Sweet Corn NBD 01, Sweet Corn NBD 02 and Sweet Corn NBD 03. In addition, products of the present invention include hybrid and inbred maize lines that are capable of producing ears and kernels having a damage rating of 2 or less or 1 or less.

In yet another aspect, the present invention includes comprising hybrid maize plants, plant materials and seed having a genetic background comprising SNPs or indels including one or more of SEQ ID NOS. 6-12.

In yet another aspect, the present invention provides a plant, plant material or seed that is produced by any one of the methods that is described above.

DETAILED DESCRIPTION OF THE PREFERRED EMBODIMENTS

Figure 1:
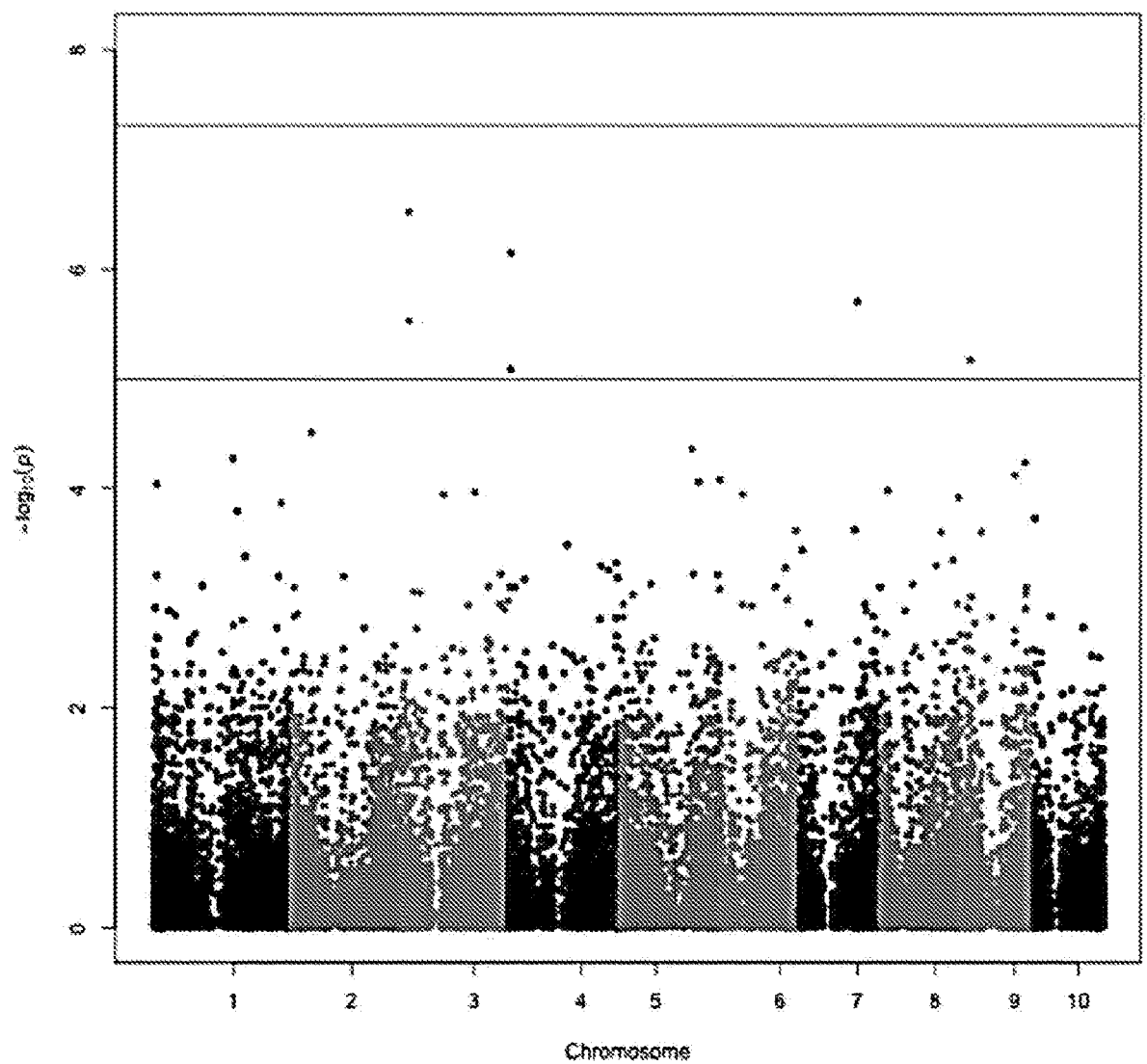
FIG. 1 is a statistical model of a genome-wide association study (GWAS) of the association of each SNP across all ten chromosomes that are present in maize plants, and using phenotypic data resulting from a first maize plant corn silk fly and phorid fly damage scoring scale ("the first scoring scale") having values ranging from 1 to 8 (Phe1-8) based upon the level of susceptibility or lack of defense of a maize plant variety to corn silk fly and phorid fly damage. In this scoring scale, a score of 1 represents a maize plant variety that is the most resistant, or has the greatest defense capabilities, to corn silk flies and phorid flies, a score of 8 represents a maize plant variety that is the most susceptible, or the least defensive, to corn silk flies and phorid flies (i.e., that is not at all resistant to corn silk flies and phorid flies), and scores of 2-7 represent varying levels of resistance (defense) and susceptibility (lack of defense) to corn silk flies and phorid flies, with more resistance (defensiveness) and less susceptibility (lack of defense) indicated by the lower numbers, and with less resistance (defensiveness) and more susceptibility indicated by the higher numbers. This GWAS analysis was performed with the data set from the first scoring scale.

The present invention may be understood more readily by reference to the following detailed description of the preferred embodiments of the invention.

Definitions

For purposes of clarity, various terms and phrases that are used throughout this specification and the appended claims are defined in the manner that is set forth below. If a term or phrase that is used in this specification, or in the appended claims, is not defined below, or otherwise in this specification, the term or phrase should be given its ordinary meaning.

The term "allele" as is used herein refers to one of multiple alternative form of a gene (one member of a pair) that is located at a specific position or locus on a specific chromosome, and controls the same phenotype (with potentially differing effects). Alleles are variants of a gene that produce different traits in a gene's characteristics, and can differ in either coding sequences or non-coding sequences.

The term "amplification" as is used herein means a process in molecular biology by which a nucleic acid molecule is enzymatically copied to generate a progeny population with the same sequence as the parental one. The most widely used amplification method is Polymerase Chain Reaction (PCR), and the result of a PCR amplification of a segment of DNA is called an "amplicon."

The term "backcross" as is used herein means to cross (a hybrid or other plant) with one of its parents, or with an individual that is genetically identical or similar to one of its parents.

The phrases "blank tip" and "blank ear tip" as are used herein mean the tip of a maize ear (one or a plurality of rows on that end of the ear that is opposite to the end that is adjacent with the stalk in which kernels would typically be present) that has little or no physical indication that one or a plurality of kernels were ever developed (i.e., it is missing one or a plurality of kernels in that area of the corn ear). Blank ear tips, which are missing kernels, may result from environmental stress factors and/or insect pest feeding thereon, and typically render the maize ear undesirable to maize purchasers and consumers (the ear is not complete in regard to kernels and, thus, it has an undesirable appearance and fewer kernels for consumption).

The term "breeding" as is used herein means the science and/or art of manipulating the heredity of an organism for a specific purpose.

The terms "control" or "controlling" as used herein mean the ability of a maize plant to prevent, or assist in preventing, damage from insects, such as armyworm, corn silk fly and phorid fly.

The terms "corn" and "maize" as is used herein means any of numerous cultivated forms of a widely grown, usually tall annual cereal grass (*Zea mays*) bearing grains or kernels on large ears, and includes the numerous varieties of sweet corn and supersweet corn. The grains or kernels of this plant may be used as food for humans and livestock, or for the extraction of an edible oil or starch. The kernels of sweet corn may be eaten raw or cooked, and may be canned, frozen and/or stored in other manners that are known by those of ordinary skill in the art.

The term "crop" as is used herein means the periodic, such as annual, bi-annual, quarterly, seasonal, or the like, yield of any plant that is grown in significant quantities to be harvested as food, as livestock feed, as fuel or for any other economic (or other) purpose. Many types of crops are used for industrial purposes, for example, they are grown and harvested for the sole purpose of making profit and feeding people, and are grown in large quantities in certain areas that are suitable for growing crops. That which is considered to be "seasonal" in one geographic region, such as a town, city, county, state, country or continent, may not be considered to be "seasonal" in a different such geographic region, and vice versa.

The terms "cross," "crossing," "interbreeding" and "crossbreeding" as are used herein mean the act of breeding different species or varieties of plants to produce hybrids.

The phrase "damage rating scale" as is used herein refers to the description of the level of damage attributable to insects, including armyworm, corn silk fly and phorid fly, to the ear and/or kernel of a maize plant using the numerical rating scale that is set forth in Table 3.

The terms "defend" or "defense" as used herein mean the ability of a maize plant to protect itself, or to be protected, from or against damage from insects, such as armyworm, corn silk fly and phorid fly.

The term "dominant" as is used herein means an allele or a gene that is expressed in an organism's phenotype, generally masking the effect of the recessive allele or gene, when present. Usually, a dominant allele is symbolized with a capital letter, and a recessive allele is symbolized with a small letter, for example: Hh (where H refers to the dominant allele and h refers to the recessive allele).

The phrases "DNA probe," "gene probe" and "probe" as are used herein mean a single-stranded DNA molecule used in laboratory experiments to detect the presence of a complimentary sequence among a mixture of various single-stranded DNA molecules.

The phrase "DNA sequencing" as is used herein means a determination of the order of nucleotides in a specific DNA molecule.

The term "endosperm" as is used herein means the nutritive tissue that is found in many seeds of plants, and that surrounds the embryo within such seeds. It supplies nutrients to the embryo.

The term "express" as is used herein means to manifest the effects of a gene, to cause to produce an effect or a phenotype, or to manifest a genetic trait, depending upon the context. The expression of a gene is the translation of information encoded in the gene into protein or ribonucleic acid (RNA).

The term "F1 hybrid" as is used herein means the first filial generation of offspring of distinctly different parental types.

The term "gene" as is used herein refers to the basic unit of heredity (genetic traits) in a living organism (plant, animal or micro-organism) that holds the information that is required to pass genetic traits to offspring. It is a segment of deoxyribonucleic acid (DNA) that contributes to a phenotype/function. The DNA is a molecule in the shape of a double helix, with each rung of the spiral ladder having two paired bases selected from adenine (A), thymine (T), cytosine (C) or guanine (G). Certain bases always pair together (AT and GC), and different sequences of base pairs form coded messages. Genes are arranged in precise arrays all along the length of chromosomes, which are much larger structures.

The phrase "gene expression" as is used herein means the process in which a cell produces the protein and, thus, the characteristic, that is specified by a gene's nucleotide sequence.

The phrase "genetic map" as is used herein means a diagram that shows the genetic linkage relationships among loci on chromosomes (or linkage groups) within a given species. "Mapping" is the process of defining the linkage relationships of loci through the use of genetic markers, populations that are segregating for such markers, and standard genetic principles of recombination frequency. A "map location" is a specific locus on a genetic map where an allele can be found within a given species.

The phrase "genetic marker" as is used herein means a specific fragment of DNA that can be identified within a whole genome. It is a genetic factor that can be identified and, thus, act to determine the presence of genes or traits linked with them, but not easily identified.

The term "genome" as is used herein means the complete set of genes in an organism, such as a plant, or the total genetic content in one set of chromosomes, depending upon the context. It is the complete set of chromosomes found in each cell nucleus of an individual or organism.

The phrase "genome-wide association study" or "GWAS" as is used herein means an examination of genetic variation across the genomes of different individuals to identify a genetic association with a particular phenotypic trait. A GWAS may be performed by collecting quantitative phenotypic data and genome-wide SNP data and determining which SNPs have a high degree of association with the phenotypic trait.

The term "genotype" as is used herein refers to the set of genes in the DNA of an organism, plant, animal, or the like, that is responsible for a particular trait (i.e., inherited instructions that is carried within its genetic code). A genotype is the specific combination of alleles present at a single locus in the genome, and can only be determine by biological testing, not by observation.

The term "germplasm" as is used herein means the living genetic resources, such as seeds or tissue, that is maintained for the purpose of animal and plant breeding, preservation, and other research uses.

The term "harvest" as is used herein means the gathering (collecting and/or assembling) of a crop of any kind, for example, of maize.

The phrase "health conscious" as is used herein means concern by an individual about the degree of health of the individual's diet and/or lifestyles, with the term "health" referring to a state of preferably complete physical, mental and/or social well-being and/or an absence of malady, disease, defect or infirmity.

The term "heterozygous" as is used herein means having dissimilar alleles that code for the same gene or trait. It is a situation in which the two alleles at a specific genetic locus are not the same. An example is a zygote having one dominant allele and one recessive allele, i.e., Aa, for a particular trait.

The term "heterozygosity" as is used herein means the presence of different alleles at one or more loci on homologous chromosomes.

The term "homologous" as is used herein in connection with chromosomes means those that contain identical linear sequences of genes, and which pair during meiosis. It means stretches of DNA that are very similar in sequence, so similar that they tend to stick together in hybridization experiments. Each homologue is a duplicate of one of the chromosomes contributed by one of the parents, and each pair of homologous chromosomes is normally identical in shape and size. Homologous can also be used to indicate related genes in separate organisms controlling similar phenotypes.

The phrase "homologous chromosomes" as is used herein means a pair of chromosomes containing the same linear gene sequences, each derived from one parent.

The term "homozygous" as is used herein means a situation in which two alleles at a specific genetic locus are identical to one another.

The term "homozygosity" as is used herein means the presence of identical alleles at one or more loci (a specific place on a chromosome where a gene is located.) in homologous chromosomal segments.

The term "husk" as is used herein means the outer leafy protective covering of an ear of maize.

The term "hybrid" as is used herein means an offspring or progeny resulting from a cross between parents of two different species, sub-species, races, cultivates or breeding lines (i.e., from crossbreeding). A single-cross hybrid is a first generation of offspring resulting from a cross between pure bred parents. A double-cross hybrid is offspring resulting from a cross between two hybrids of single cross. A three-way cross hybrid is offspring from a cross between a single-cross hybrid and an inbred line. A triple-cross hybrid is offspring resulting from the crossing of two different three-way cross hybrids.

The term "inbred" as is used herein means offspring produced by inbreeding (succeeding generations of organisms, such as plants, that are all derived by breeding from the same group of closely related organisms). When lines are inbred sufficiently, a homozygous condition of particular alleles can generally be assumed.

The term "inbreeding" as is used herein means the breeding of plants, plant materials or organisms that are related, depending upon the context (i.e., of plants, plant materials or organisms within an isolated or a closed group of plants, plant parts or organisms). It is the continued breeding of closely related plants, plant parts or organisms, so as to preserve desirable traits therein.

The term "indel" as is used herein means a short polymorphism that corresponds to the insertion, deletion, or insertion and deletion of a small number of nucleotides in a genomic DNA sequence.

The term "insect" as is used herein means any of a class of invertebrates within the arthropod phylum that have a chitinous exoskeleton, a three-part body (head, thorax and abdomen), three pairs of jointed legs, compound eyes and/or one pair of antennae, and possibly wings.

The term "insect damage" as is used herein means damage to a plant or a plant part, including the ear and silk of a maize plant, resulting from insects including, armyworm, corn silk fly and phorid fly.

The term "introgression" as is used herein means the transfer of genetic information from one species to another as a result of repeated backcrossing of the hybrid with one of its parental species.

The term "isogenic" as is used herein means having substantially the same genotype (i.e., genetically uniform), as all organisms produced by an inbred strain.

The terms "library," "DNA library" and "gene library" as are used herein refer to a plurality or collection of DNA fragments of one or more organisms, each generally carried by a plasmid or virus and cloned into an appropriate host. A DNA probe is generally used to locate a specific DNA sequence in the library. A collection representing the entire genome of an organism is known as a genomic library, and an assortment of DNA copies of messenger RNA produced by a cell is known as a complimentary DNA (cDNA) library.

A "linkage map" as is used herein means a map of the relative positions of genetic loci on a chromosome, determined on the basis of how often the loci are inherited together. Distance may be measured in centimorgans (cM).

The term "line" as is used herein means a population, breed or strain of an organism, plant or animal. A "pure line" is a population, breed or strain of an organism, plant or animal that maintains a high degree of consistency in certain characters as a result of inbreeding for generations.

The term "locus" as is used herein refers to a specific chromosome location in the genome of a species where a specific type of gene can be found. It is the position on the chromosome where the gene for a particular trait resides. A locus may be occupied by any one of several alleles (variants) for a given gene.

The phrase "molecular marker" as is used herein means a specific fragment of DNA that can be identified within a whole genome. It is an identifiable physical location on a chromosome (i.e., restriction enzyme cutting site, gene, or the like) whose inheritance can be monitored. Molecular markers are generally found at specific locations of a genome, and are used to 'flag' the position of a particular gene or the inheritance of a particular characteristic. In a genetic cross, the genes producing characteristics of interest will usually stay linked with the molecular markers in relatively close proximity on the chromosome. Thus, varieties can be selected in which the molecular marker is present, since the marker indicates the presence of the desired characteristic. Examples of molecular markers include simple sequence repeats (SSRs), SNPs, randomly amplified polymorphic DNA (RAPDs), and restriction fragment length polymorphisms (RFLPs). Additional information about the use of molecular markers for use in characterizing and identifying maize inbred lines, validating pedigree and showing associations among inbred lines is present in J. S. Smith et al., "An Evaluation of the Utility of SSR loci as Molecular Markers in Maize (*Zea Mays* L.): Comparisons with Data from RFLPS and Pedigree," Theor Appl Genet 95:163-173 (1997). Microsatellites, or SSRs are relatively short nucleotide sequences, usually from two to three bases in length that are generally repeated in tandem arrays. Amplifiable polymorphisms are revealed because of differences in the number of tandem repeats that lie between sequences that are otherwise conserved for each locus. Microsatellite loci are highly polymorphic and are useful as genetic markers in many plant species, including maize.

The term "mutation" as is used herein refers to a permanent, heritable change of genetic material, either in a single gene or in the numbers or structures of the chromosomes.

The term "NILs" as is used herein means near isogenic lines, which are lines of a plant, such as sweet corn, that are genetically identical, except for one locus or a few loci.

The term "nucleotide" as is used herein means the basic building block (subunits) of nucleic acids, such as DNA and RNA. It is an organic compound that is generally made up of nitrogenous base, a sugar and a phosphate group. DNA molecule consists of nucleotides in which the sugar component is deoxyribose, whereas the RNA molecule has nucleotides in which the sugar is ribose. The most common nucleotides are divided into purines and pyrimidines based upon the structure of the nitrogenous base. In DNA, the purine bases include adenine and guanine, while the pyrimidine bases are thymine and cytosine. RNA includes adenine, guanine, cytosine and uracil instead of thymine. Aside from serving as precursors of nucleic acids, nucleotides also serve as important cofactors in cellular signaling and metabolism. These cofactors include flavin adenine dinucleotide (FAD), flavin mononucleotide, adenosine triphosphate (ATP) and nicotinamide adenine dinucleotide phosphate (NADP). To form a DNA or RNA molecule, generally thousands of nucleotides are joined together in a long chain. A DNA oligonucleotide is a short piece of DNA composed of relatively few (oligo-) nucleotide bases.

The phrase "null hypothesis" as is used herein means a hypothesis which a researcher tries to disprove, reject or nullify.

The abbreviation "PCR" as is used herein means "polymerase chain reaction," which is a technique used in molecular biology to amplify a single copy, or a few copies, of a piece of DNA (a focused segment of DNA) across several orders of magnitude, generating thousands to millions of copies of a particular DNA sequence. It is a well-known technique by those having ordinary skill in the art for replicating a specific piece of DNA in vitro, even in the presence of excess non-specific DNA. Primers are added (which initiate the copying of each strand) along with nucleotides and heat stable Taq polymerase. By cycling the temperature, the target DNA is repetitively denatured and copied. Because the newly synthesized DNA strands can subsequently serve as additional templates for the same primer sequences, successive rounds of primer annealing, strand elongation, and dissociation produce rapid and highly specific amplification of the desired sequence. PCR also can be used to detect the existence of the defined sequence in a DNA sample. A single copy of the target DNA, even if mixed in with other undesirable DNA, can be amplified to obtain billions of replicates. PCR can be used to amplify RNA sequences if they are first converted to DNA via reverse transcriptase. PCR buffers, primers, probes, controls, markers, amplification kits, sDNA synthesis kits, general PCR kits, and the like are available from sources that are known by those having ordinary skill in the art, such as Applied Biosystems (Foster City, Calif.), and may readily be used by those having ordinary skill in the art in accordance with the present invention.

The phrase "PCR primer" as is used herein means a short segment of DNA or RNA that is complementary, and hydrogen bonded, to a given DNA sequence, and that is needed to initiate replication by DNA polymerase. It is used to start the PCR process, and acts as a point at which replication can proceed.

The term "pest" as is used herein means an animal or insect that is annoying, troublesome, detrimental, harmful, a nuisance, attacks, and/or causes damage or destruction, for example, to plant crops or livestock.

The term "pericarp" as is used herein means the wall of a plant fruit, such as a corn kernel, which generally is developed from an ovary wall, and contains an outer exocarp, a central mesocarp and an inner endocarp.

The term "phenotype" as is used herein means an observable characteristic or trait of an organism, such as sweet corn, such as its morphology, development and/or biochemical or physiological properties. It is a biological trait or characteristic possessed by an organism (including a plant) that results from the expression of a specific gene. Phenotypes generally result from the expression of an organism's genes, as well as the influence of environmental factors, and possible interactions between the two. In natural populations, most phenotypic variation is continuous, and is effected by alleles at one or multiple gene loci.

The term "pollen" as is used herein means the fine powder-like material consisting of pollen grains that contain the male reproductive cells of most plants. Pollen is generally produced by the anthers of seed plants.

The term "pollination" as is used herein means the process by which plant pollen is transferred, generally from the anther to the stigma (from male reproductive organs to the female reproductive organs) of a plant flower to produce offspring (to form seeds). In flowering plants, pollen is transferred from the anther to the stigma, often by the wind or by insects. In cone-bearing plants, male cones release pollen that is usually borne by the wind to the ovules of female cones. The pollen grain generally contains two cells: a generative cell and a tube cell. The generative nucleus generally divides to form two sperm nuclei. The tube cell generally grows down into the pistil until it reaches one of the ovules contained in the ovary. The two sperm generally travel down the tube and enter the ovule, where one sperm nucleus generally unites with the egg. The other sperm nucleus generally combines with the polar nuclei that exist in the ovule, completing a process known as "double fertilization." These fertilized nuclei then generally develop into the endocarp, the tissue that feeds the embryo. The ovule itself generally develops into a seed that is contained in the flower's ovary (which ripens into a fruit). In gymnosperms, the ovule is exposed (not contained in an ovary), and the pollen produced by the male reproductive structures lands directly on the ovule in the female reproductive structures.

The term "polymorphism" as is used herein means an ability to exist in more than one form, such as several different forms, and particularly two or more clearly different phenotypes existing in the same population of a species.

The term "polynucleotide" as is used herein means an organic polymer molecule that is composed of nucleotide monomers covalently bonded in a chain. DNA and RNA are examples of polynucleotides that have a distinct biological function.

The term "primer" as is used herein means a relatively short pre-existing polynucleotide chain to which new deoxyribonucleotides can be added by DNA polymerase.

The phrases "probes" and "hybridization probes" as are used herein mean a fragment of DNA or RNA of a variable length (usually 100-1000 bases long) which can be radioactively labeled, and can then be used in DNA or RNA samples to detect the presence of nucleotide sequences (the DNA target) that are complementary to the sequence in the probe. The probe thereby hybridizes to single-stranded nucleic acid (DNA or RNA) whose base sequence allows probe-target base pairing due to complementarity between the probe and target. The labeled probe is first denatured (by heating or under alkaline conditions such as exposure to sodium hydroxide) into single stranded DNA (ssDNA) and then hybridized to the target ssDNA (Southern blotting) or RNA (Northern blotting) immobilized on a membrane or in situ.

The term "protect" as is used herein means to keep or prevent something (or someone) from causing injury, harm, damage or other adverse consequences to, for example, an organism, plant, animal or human being.

The term "protein" as is used herein refers to a large molecule composed of one or more chains of amino acids in a specific order, which is determined by the base sequence of nucleotides in the gene that is coding for the protein. Proteins are required for the structure, function, and regulation of cells, and each protein has unique functions.

The term "provide" as is used herein means to supply, or make available, a characteristic, a quality, a thing or the like, that is wanted or needed, and which previously was not available.

The term "p-value" as is used herein means the probability of obtaining a result equal to or more extreme than what was actually observed, when the null hypothesis is true. The p-value is widely used in statistical hypothesis testing, specifically in null hypothesis significance testing.

The phrase "quantitative trait locus" (QTL) as used herein means a section of DNA (the locus) that correlates with variations in a phenotype. QTLs are mapped by identifying which molecular markers (such as SNPs) correlate with an observed trait.

The term "recessive" as is used herein in connection with a gene means a gene whose phenotypic effect is expressed in the homozygous state, but is masked in the presence of the dominant allele (i.e. when the organism is heterozygous for that gene). It is a phenotype that is expressed in organisms (including plants) only if it is homozygous for the corresponding allele. Usually the dominant gene produces a functional product whereas the recessive allele does not: both one dose and two doses per nucleus of the dominant allele, therefore, generally lead to an expression of its phenotype, whereas the recessive allele is generally observed only in the complete absence of the dominant allele.

The phrase "recurrent parent" as is used herein means the parent to which a hybrid is crossed in a backcross. If the recurrent parent has an elite genotype, at the end of a backcrossing program, an elite genotype is typically recovered.

The term "restriction enzyme" as is used herein means a protein (enzyme) produced by bacteria that cuts DNA at or near specific recognition nucleotide sequences known as restriction sites (i.e., it acts like scissors).

The term "seed" as is used herein means a propagating organ formed in the sexual reproductive cycle of gymnosperms and angiosperms (male and female sex cells) that includes a protective coat enclosing an embryo and food reserves. It is a small hard fruit that is generally located in a fertilized ovule of a plant. A seed has two main components, the embryo and the endosperm. The endosperm acts as a food store for the embryo which, over time, will grow from this rich food supply that enables it to do so. The seed contains an embryo and, in most plants, stored food reserves wrapped in a seed coat. Under favorable growth conditions, a seed begins to germinate, and the embryonic tissues resume growth, developing towards a seedling.

The term "selection" as is used herein means the preferential survival and reproduction, or preferential elimination, of individuals with certain genotypes (genetic compositions) by means of natural or artificial controlling factors.

The term "selfing" as is used herein means manually pollinating a plant by placing its pollen on its own stigma.

The term "self-pollination" is as used herein refers to the transfer of pollen from the anther to the stigma of the same flower, another flower on the same plant, or the flower of a genetically identical plant.

The term "silk" as is used herein in regard to maize means the long filamentous styles and stigmas that appear as a silky tuft or tassel at the tip of an ear of corn.

The abbreviation "SNP" as is used herein means "single nucleotide polymorphism," and is a DNA sequence variation occurring when a single nucleotide (A, T, C, or G) in the genome (or other shared sequence) differs between members of a species (or between paired chromosomes in an individual). For example, at a specific base position in the human genome, the base C may appear in most individuals, but in a minority of individuals, the position is occupied by base A. There is a SNP at this specific base position, and the two possible nucleotide variations (C or A) are said to be alleles for this base position.

The phrase "test cross" as is used herein means the crossing of an organism, such as a plant, with an unknown genotype, to a homozygous recessive organism (tester). It is a cross between an individual of unknown genotype or a heterozygote (or a multiple heterozygote) to a homozygous recessive individual.

The term "transcription" as is used herein means the synthesis of RNA under the direction of DNA. RNA synthesis, or transcription, is the process of transcribing DNA nucleotide sequence information into RNA sequence information. Both nucleic acid sequences use complementary language, and the information is simply transcribed, or copied, from one molecule to the other. DNA sequence is enzymatically copied by RNA polymerase to produce a complementary nucleotide RNA strand (messenger RNA or mRNA) because it carries a genetic message from the DNA to the protein-synthesizing machinery of the cell.

The term "translation" as is used herein means the process by which polypeptide chains are synthesized, the sequence of amino acids being determined by the sequence of bases in a messenger RNA, which in turn is determined by the sequence of bases in the DNA of the gene from which it was transcribed.

The term "whorl" as is used herein means a configuration of a maize plant just prior to an extrusion of its tassel (i.e., when the leaves are very concentrated, and there are multiple layers of them, and the tassel will soon be visible, and the internotes of the plant will elongate).

The term "wholesome" as is used herein in regard to maize means not unhealthy for the human or animal body, or healthy for the human or animal body (i.e., contributing to, enhancing, promoting or providing physical, mental and/or emotional well-being).

The term "wild-type" as is used herein refers to a native or predominant genetic constitution before mutations, usually referring to the genetic constitution normally existing in nature.

The term "yield" as is used herein refers to plant, plant material and/or seed productivity, such as the productivity per unit area of a particular plant product of commercial significance.

DESCRIPTION OF THE INVENTION

The following description illustrates the methods and products of the present invention. The description is intended to be merely illustrative of the present invention, and not limiting in either scope or spirit. Those of ordinary skill in the art will readily understand that variations of certain of the conditions and/or steps employed in the procedures described herein can be employed. While these procedures have been performed using sweet corn kernels and plants, the same procedures that are described may be employed with other members of the maize family, including field, flint, flour, dent, pop, waxy and pod corn.

The present invention may be understood more readily by reference to the following detailed description of the steps undertaken to provide a means for controlling and defending against the corn silk fly and phorid fly in maize plant lines, and means of testing and identifying the presence of the genes responsible for controlling and defending against the corn silk fly and phorid fly. The following detailed description also describes the products of the invention that incorporate the genes responsible for those control and defense mechanisms.

Procurement of Maize Parent Inbred Lines for Crossing and Initial Selections

Maize inbred lines designated IN 705, IN 706 and IN 714 were obtained from Dr. W. Paul Williams, Supervisory Research Geneticist USDA-ARS, Corn Host Plant Resistance Unit (CHPRU) (Mississippi State, MS). These inbred lines are all dent corn inbred lines and are publicly available from the CHPRU at Mississippi State, MS. Sixteen maize inbred lines from Abbott & Cobb's (Feasterville, Pa.) sweet corn breeding program, including AC 194, BL 6440 (181MR) and AC 232Y, were then selected for backcrossing into these dent corn lines.

Breeding Protocol for Maize Inbred Parent Lines

The maize inbred parent lines identified in TABLE 1 below were backcrossed and self-pollinated at the Everglades Research and Education Center, IFAS, University of Florida (Belle Glade, Fla.) or at the Abbott & Cobb, Inc. (A&C) Research Breeding Station (Loxahatchee, Fla.), in the manner described in TABLE 2. Because dent corn possesses many traits that are not suitable for sweet corn (which must be sweet and must maintain its sweetness and delay or reduce conversion of sugars to starches in order to be palatable and acceptable to consumers), the selection process required a focus not only on identifying insect protection efficacy but rigorous selection for the necessary sweet corn horticultural attributes to make the corn acceptable to consumers. Utilizing these selection criteria, the progeny of AC 194, BL 6440 (181MR) and AC 232Y (out of the sixteen maize inbred lines initially chosen from A&C's sweet corn breeding program) were ultimately selected for further inbred line development.

TABLE 2 shows the maize breeding protocol for backcrossing and selection of the parent inbred lines obtained from the sources described in TABLE 1.

TABLE 1

Donor Maize Parent Inbred Lines

| Designation | Source | Type |
| --- | --- | --- |
| IN 705 | CHPRU | Dent |
| IN 706 | CHPRU | Dent |
| IN 714 | CHPRU | Dent |
| AC 194 | A&C | Sweet |
| BL6440 (181MR) | A&C | Sweet |
| AC 232Y | A&C | Sweet |

TABLE 2

Breeding Protocol

| Step | Activity | Result |
| --- | --- | --- |
| 1 | A&C commercial sweet corn parent inbred line X dent corn parent inbred line (TABLE 1) | F1 Hybrid |
| 2 | F1 - Backcrossed to recurrent parent (A&C commercial parent inbred line) | BC1 (Back-Cross 1) |
| 3 | Self-pollination of BC1 | S1 (Self-Pollination 1) |
| 4 | Field insect protection efficacy testing via natural corn silk fly infestation including selection for horticultural attributes | Unsuccessful Inbred Lines Eliminated |
| 5 | Continued backcrossing to the recurrent parent and self-pollination combined with field insect protection efficacy testing with natural corn silk fly and phorid fly infestation including selection for sweet corn horticultural attributes | BC2-BC6 and S2-S6 |
| 6 | Repetition of breeding listed above until six backcross generations were completed and reconstitution of the recurrent parents was considered genetically stable, uniform and complete | Successful Inbred Lines |

Plantings of Parent Inbred Lines and Developed Hybrid Lines in Test Nurseries

The initial crosses of the dent corn inbred parent lines and the sixteen sweet corn inbred lines, the backcrossing of the initial F1 hybrids with the recurrent sweet corn inbred lines, and all further backcrossing and recurrent selections described in steps 1, 2, 4, 5 and 6 of TABLE 2, were performed in the test nurseries at Belle Glade or Loxahatchee, Fla. The nurseries consisted of fifty single rows, approximately 25 feet long, each containing about 30 plants. The plant spacing within the rows was approximately 8 to 8½", and the spacing between (or width of) the rows was about 30". The plantings were staged so that pollination occurred during the times of the season in Florida when corn silk flies and phorid flies were most prevalent (i.e., "natural" infestation was employed). Damage assessments were made from the time the plants were in the whorl state until the time of the final ear harvest. No chemical pesticides and/or insecticides were applied aerially, on the ground, or otherwise to any of the maize plants, and/or to any other surroundings to control the corn silk fly and phorid fly populations at either location.

Damage Rating Scale and Phenotypic Analyses of Resulting Maize Plant Ears and Kernels A damage rating scale was developed to evaluate the extent of damage to the ears and kernels of a maize plant attributable to insect damage to the maize plant ears and ear tips and maize kernels, and to assist in making selections during the recurrent selection breeding process.

The damage rating scale was a survey-type phenotypic scale that included nine discrete categories, or injury classes, ranging from "0" to "8," with a focus on the maize plant ear tips. The damage rating scale measured the depth of insect feeding from the tip of the ear downwards towards the stalk. The maize plant ears and kernels were rated at the maturity stage of the ear.

The damage rating scale was developed within the framework and assumptions of Poisson Distribution. Poisson Distribution is well known to those of ordinary skill in the art. (See R. G. D. Steel et al., "Principles and Procedures of Statistics: A Biometrical Approach," McGraw-Hill Publ. Co., New York, 2nd ed., ISBN 0-070-60926-8, 629 (1980)); and G. W. Snedecor et al., "Statistical Methods," Iowa State Univ. Press, Ames, 7th ed., ISBN 0-813-81560-6, 505 (1980).) To establish the damage rating scale, precise metrics and numerical values were assigned to the insect damage that was visually observed to both the ears and kernels of the maize plants.

TABLE 3 below shows the damage rating scale developed, and utilized, to evaluate and rate the maize plants described in Steps 1, 2, 4, 5 and 6 of TABLE 2 in terms of insect damage and to assist in the selection of maize parent lines and maize hybrids. Ears that received a rating of "0" or "1" are considered to be commercially acceptable to consumers and seed from those ears was selected for use in further breeding efforts to produce maize parental inbred lines. Ears that received ratings of 2-8 are considered to have too much insect damage to be commercially acceptable to consumers and were therefore not selected to be used in further breeding efforts.

TABLE 3

Ear and Kernel Phenotypic Insect Damage Rating Scale
(25 Ears/Row Average)

| Maize Ear/Kernel Damage | Rating Scale |
| --- | --- |
| No Damage To Any Ears | 0 |
| Less than 30 mm Damage to Ear Tips of 1-3 Ears | 1 |
| Less than 30 mm Damage to Ear Tips of 4-6 Ears | 2 |
| Ear Tip Damage to 4-7 Ears Extending from the First to Third Kernel | 3 |
| Ear Tip Damage to 4-7 Ears Extending from the First to Fourth Kernel | 4 |
| Ear Tip Damage to 7-10 Ears Extending from the First to Fourth Kernel | 5 |
| Ear Tip Damage to 7-10 Ears Extending from the First to Sixth Kernel | 6 |
| Ear Tip Damage to All Ears With the Majority of Ears Having Kernel Damage Beyond the Fourth to Sixth Kernel | 7 |
| Ear Tip Damage to All Ears with all Ears Having Kernel Damage Beyond the Fourth to Sixth Kernel | 8 |

The above damage rating scale is independent of any standards for fresh produce used by the Agricultural Marketing Service of the United States Department of Agriculture (USDA).

Genotypic Analyses of Resulting Leaf Tissue Samples

Based on the damage rating scale in TABLE 3, numerous selections were made to identify the maize plants within each row that achieved the highest level of insect protection. Leaf tissue samples were only taken from the best (highest rated) (rated as a "0" and "1" in TABLE 3) of the above lines, as well as those that were the lowest rated (for a relative comparison) (those rated as a "7" or "8" in TABLE 3). Approximately 10-15 leaf tissue samples from each row were provided to RAPiD Genomics (Gainesville, Fla.), which was contracted to provide commercial genome sequencing services. Initially, 881 leaf tissue samples were provided to RAPiD Genomics for purposes of performing a GWAS to identify the genes associated with the control of and defense against insects that had been observed in testing plots. From these 881 leaf tissue samples, the samples were reduced to 784 tissue samples using phenotypic information regarding desired horticultural characteristics.

RAPiD Genomics utilized its genotyping method called "Capture-Seq" to identify the DNA markers having significant association with the control of and defense against insect damage across all ten maize chromosomes present in the 784 leaf tissue samples. Using methods known to those of ordinary skill in the art, DNA was extracted from each of the 784 leaf tissue samples. The extracted DNA was then fragmented using known methods to an average size of 300 bp using ligases (enzymes). Next-Generation Sequencing libraries were then prepared.

A total of 837,779 probes were designed in 39,024 protein-coding genes annotated in the well-known B73 maize cultivar. These probes were filtered to obtain high-quality baits, resulting in 60,433 probes. Out of the 60,433 probes, 5,000 were randomly chosen limiting the selection to one probe per gene. In addition, a set of probes was designed to target peptidase and inhibitor genes in maize. After filtering, 617 additional high quality probes were designed, resulting in 5,617 probes for use in hybridizing target areas of interest in the 784 tissue samples.

The Next-Generation Sequencing libraries prepared from the DNA extracted from the 784 leaf tissue samples were then hybridized against the 5,617 probes, and the enriched product was sequenced on an Illumina platform (2×100 bp mode). The resulting raw DNA sequencing data were processed in a bioinformatics pipeline using common techniques—read quality filtering, data alignment against the B73 reference genome, and Bayesian variant culling at the population level, resulting in the identification of a total of 46,069 SNPs. The resulting SNP data was then adjusted in the GWAS analysis for association with the phenotypic information derived from the damage rating scale data.

The phenotypic data generated from the insect damage rating scale (TABLE 3) was used to create two scoring scales to be used in the GWAS analysis. The first insect damage scoring scale ranged from 1-8 (Phe 1-8) ("the first scoring scale"), in which a score of 1 indicated a maize plant that had the highest level of insect defense and a score of 8 indicated a maize plant that was the most susceptible (least protected or had the least amount of defense) to damage.

In addition, a second scoring scale was established to create a binary trait for purposes of the GWAS analysis ("the second scoring scale") by: 1) recoding and grouping all plants having scores of 0 or +1 under the first scoring scale together (i.e., by giving a score of "0" to those maize plants that had a rating of either 0 or 1 in the first scoring scale); and 2) recoding and grouping together every maize plant having a rating score greater than 1 on the first scoring scale a score of "1" (PheBIN).

Both phenotype data sets were then analyzed independently as dependent variables of a mixed linear regression model, testing the association level of each SNP with the phenotype (TABLE 3). A relationship matrix built from the markers was also adjusted in the model to correct for population structure. The p-values for each marker were calculated to infer the probability of association of that marker with the given attribute (highest defense to damage).

All of the SNPs were adjusted in a GWAS analysis to test for an association with both phenotypic data sets from the two phenotype scoring scales (Phe1-8 and PheBIN). The resulting data were then used to identify candidate QTL regions.

GWAS Analyses

FIG. 1 is a representation of a statistical model of a GWAS showing an association of each of the above SNPs across all ten chromosomes in maize plants. This GWAS analysis was conducted with the data set discussed above in connection with the first scoring scale (Phe1-8). In FIG. 1, the x-axis represents the location of each SNP across the ten maize plant chromosomes relative to the SNP's association with insect damage defense based upon its phenotypic scoring. The y-axis illustrates the relative probability (−log of the p-values) of each such SNP.

Figure 2:
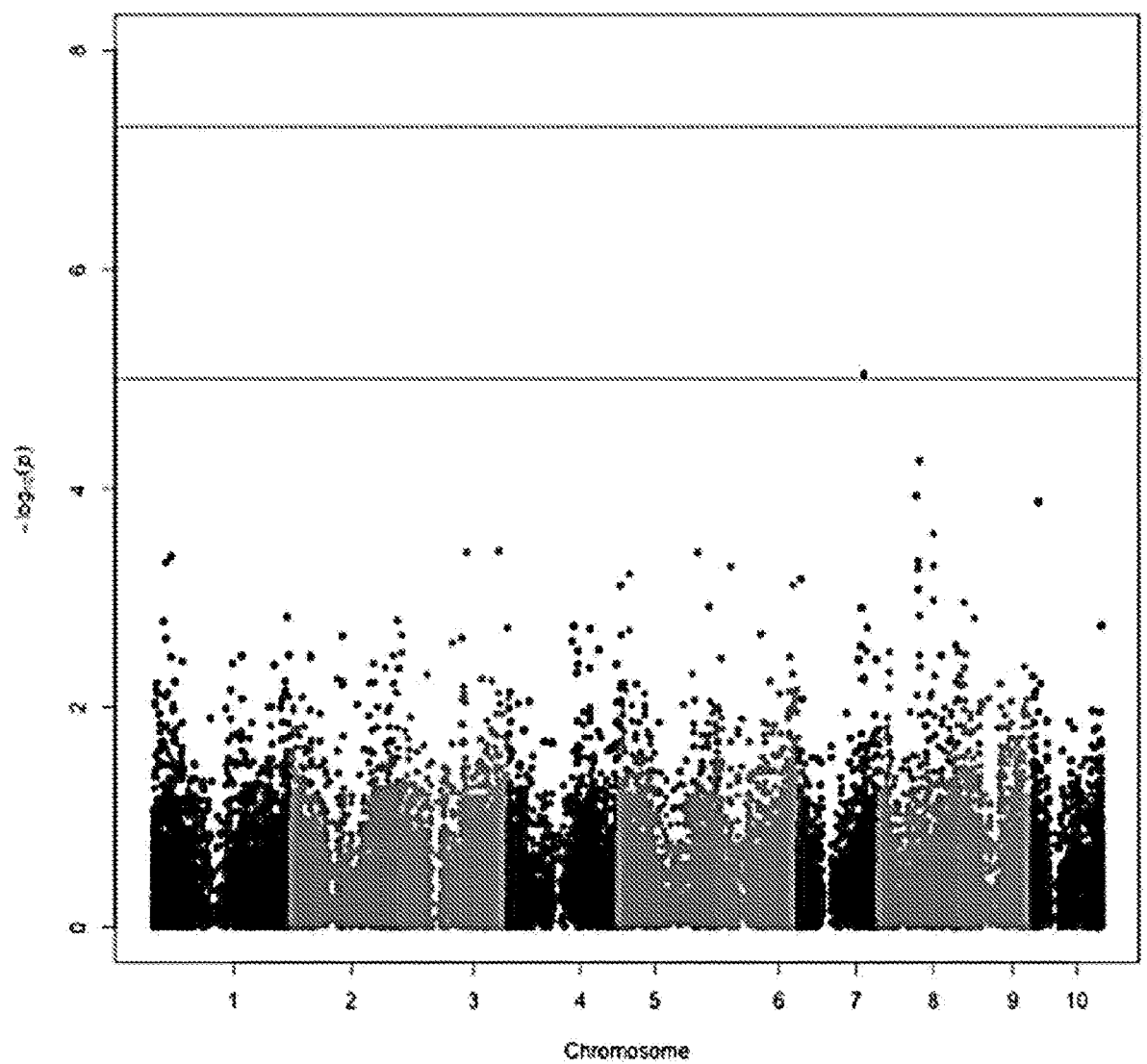
FIG. 2 is a statistical model of a GWAS of the association of each SNP across all ten chromosomes that are present in maize plants, and using phenotypic data resulting from a second maize plant corn silk fly and phorid fly damage scoring scale ("the second scoring scale") in which the above-described first scoring scale was recoded to create a binary data set necessary for the statistical analysis model, which requires a binary logarithmic application, and has a score of either 0 or +1, and grouping together in the +1 group every maize plant having a score in the first scoring scale of greater than 1 (PheBin). This GWAS analysis was performed with the binary data set from the second scoring scale.

FIG. 2 is a representation of a statistical model of a GWAS showing an association of each of the above SNPs across all ten chromosomes present in maize plants. This GWAS analysis was conducted with the binary data set discussed above in connection with the second scoring scale (PheBIN). This GWAS analysis revealed one additional candidate QTL region.

Based on the GWAS analyses, seven SNPs having a highly positive association (associated with a p-value less than $1\times10^{-6}$) with the maize plant insect defense phenotype were identified. These seven SNPs are located on four maize chromosomes (chromosomes 3, 4, 7, and 9). QTL regions on two of these four chromosomes (chromosomes 7 and 9) were previously reported to be candidate regions for the resistance to both fall armyworm and southwestern corn borer. (Brooks et al. 2007). The identification of these same QTL regions on chromosomes 7 and 9 in the GWAS analysis substantiates the significant association between these regions of the genome and the expression of a means of controlling and defending against insect damage.

The list of SNPs corresponding to QTL regions with significant associations to maize plant insect defense phenotypes and their corresponding genes are presented on TABLE 4.

TABLE 4

SNPs having a Highly Positive Association to the Maize Plant Insect Defense Phenotype

| Maize Plant Chromosome Number | p-value | B73 Bin | Link the gene ID | SNP Designation | Alternative Alleles |
|---|---|---|---|---|---|
| 3 | 3.04E−07 | 3.04 | SEQ ID NO.: 1 | 17606436 SEQ ID NO.: 6 | C |
| 3 | 2.96E−06 | 3.04 | SEQ ID NO.: 1 | 17606457 SEQ ID NO.: 7 | TGCG |
| 4 | 8.13E−06 | 4.01 | SEQ ID NO.: 2 | 4808588 SEQ ID NO.: 8 | C |
| 4 | 7.14E−07 | 4.01 | SEQ ID NO.: 2 | 4808626 SEQ ID NO.: 9 | A |
| 7 | 1.98E−06 | 7.02 | SEQ ID NO.: 3 | 126746831 SEQ ID NO.: 10 | G |
| 7 | 9.08E−06 | 7.03 | SEQ ID NO.: 4 | 143394449 SEQ ID NO.: 11 | ATA |
| 9 | 6.76E−06 | 9.02 | SEQ ID NO.: 5 | 19033476 SEQ ID NO.: 12 | TTGCAGT |

Production of Maize Hybrids Providing Defense to Corn Silk Fly and Phorid Fly

After identifying the SNPs having a highly positive association with corn silk fly, phorid fly and other insect defense, the inbred maize plant lines containing the genes for controlling and defending against the corn silk fly and phorid fly were identified and selected for hybrid production. Maize inbred parent lines, 1115, 1118 and 1150, were identified as containing the corn silk fly and phorid fly defense genes. These inbred parent lines have been designated NBD 01, NBD 02 and NBD 03, respectively, for further breeding and hybrid production.

Maize Inbred Parent Line 1115 (NBD 01)

Maize inbred parent line 1115 (NBD 01) resulted from an initial cross of BL 6440 (181MR) with IN705-2 (BL 6440 (181MR) X IN705-2). The initial cross was made at Belle Glade, Fla. in the Spring of 2014. Backcrosses to the recurrent parent (BL 6440 (181MR)) were made in the Fall of 2014, the Spring of 2015, the Summer of 2015 in Illinois, and the Spring of 2016 in Belle Glade.

Maize Inbred Parent Line 1118 (NBD 02)

Maize inbred parent line 1118 (NBD 02) resulted from an initial cross of AC 194 with IN706-A2 (AC 194 X IN706-A2). The initial cross was made at Belle Glade, Fla. in the Spring of 2014. Backcrosses to the recurrent parent (AC 194) were made in the Fall of 2014, the Spring of 2015, the Summer of 2015 in Illinois, and the Spring of 2016 in Belle Glade.

Maize Inbred Parent Line 1150 (NBD 03)

Maize inbred parent line 1150 (NBD 03) resulted from an initial cross of AC 232Y with IN714-1 (AC 232Y X IN714-1). The initial cross was made at Belle Glade, Fla. in the Spring of 2014. Backcrosses to the recurrent parent (AC 232Y) were made in the Fall of 2014, the Spring of 2015, the Summer of 2015 in Illinois, and the Spring of 2016 in Belle Glade.

Maize Hybrids (NBDX 1001 and NBDX 1002)

Two hybrids were produced in the Spring of 2016 at the Belle Glade, Fla. nursery using 1115, 1118 and 1150 as maize inbred parent lines. The hybrid designated NBDX 1001 was produced using 1115 (NBD 01) as the female parent and 1118 (NBD 02) as the male parent. The hybrid designated NBDX 1002 was produced using 1118 (NBD 02) as the female parent and 1150 (NBD 03) as the male parent. The most desirable hybrids produced had both: (i) the highest level of corn silk fly and phorid fly defense (as evidenced by their scores on the first scoring scale); and (ii) the most favorable, commercially-required horticultural characteristics.

Maize Hybrids (NBX 2001 and NBX 2002)

In addition to maize hybrids having two parent inbred lines each of which contain the genes for controlling and defending against the corn silk fly and phorid fly, maize hybrids were produced using one parent inbred line containing the genes for controlling and defending against the corn silk fly and phorid fly and existing commercial inbred maize lines.

NBX 2001

Inbred parent line 1115 (NBD 01) was crossed with existing commercial inbred line, AC 266Y. The resulting single cross maize hybrid created using the 1115 (NBD 01) inbred line as the male parent, and AC 266Y as the female parent, designated as NBX 2001, had a score on the first scoring scale of either 0 or 1.

NBX 2002

Inbred parent line 1118 (NBD 02) was crossed with existing commercial maize line, AC 274Y ST. The resulting single cross maize hybrid varieties created using the 1118 (NBD 02) inbred line as the male parent, designated as NBX 2002, and AC 274Y ST as the female parent, designated as NBX 2002, had a score on the first scoring scale of either 0 or 1.

The specific pedigrees and the rows where the progeny were located are set forth in TABLE 5.

TABLE 5

Corn Silk Fly Defensive Hybrids Produced

| Hybrid Designation | Parent Inbred Designations | Source Rows in Nursery |
|---|---|---|
| NBDX 1001 | NBD 01 X NBD 02 | 16FF 1115 X 1118 |
| NBDX 1002 | NBD 02 X NBD 03 | 16FF 1118 X 1150 |

TABLE 5-continued

Corn Silk Fly Defensive Hybrids Produced

| Hybrid Designation | Parent Inbred Designations | Source Rows in Nursery |
|---|---|---|
| NBX 2001 | AC 266Y X NBD 01 | 16FF 1045 X 1115 |
| NBX 2002 | AC 274Y ST X NBD 02 | 16FF 1057 X 1118 |

Phenotypic Comparison with Commercially Available GMO Maize Varieties

To determine how maize varieties containing the identified SNPs compare to commercially available GMO hybrids containing insect protection traits, a comparative trial was conducted. Commercially available maize GMO hybrids from Syngenta (Boise, Id.) (GSS-0966) and Seminis (St. Louis, Mo.) (SV9010) were planted at both the Belle Glade and Loxahatchee, Fla. testing locations to make phenotypic comparisons of insect damage to the maize hybrids described above under the same insect pressure and conditions. Phenotypic information was obtained for the maize plants in each of the breeding plots. The sweet corn which was the product of the recurrent selection process described in TABLE 2 scored lower on the insect damage rating scale than the GMO maize hybrids grown under the same testing environment.

Preferred Embodiment

The preferred embodiment of the invention is one where all seven SNPs are identified as providing a means of controlling and defending against the corn silk fly and phorid fly. However, each of the seven SNPs confers some means of controlling and defending against the corn silk fly and phorid fly. Therefore, the invention is not limited to the preferred embodiment but extends to methods and products for controlling and defending against the corn silk fly and phorid fly, which incorporate one or more of the seven SNPs identified herein.

Use of SNPs as Molecular Markers for Maize Hybrid Development

Having identified the SNPs corresponding to QTL regions with significant associations to maize plant insect defense phenotypes and their corresponding genes, these SNPs can be used in marker assisted breeding and introgression strategies to reduce the time for and increase the efficiency of producing new maize parental inbred lines and maize hybrids having the means for controlling and defending against the corn silk fly and phorid fly. The use of molecular markers for the purpose of more efficiently producing parental plant lines is well known and described in the art. Identification of the relevant SNPs is frequently the limiting factor in using molecular markers that are responsible for the desired characteristic to be introduced. The present invention identifies the relevant SNPs that provide a means of controlling and defending against the corn silk fly and phorid fly, which were not known prior to the invention.

Identification of the seven SNPs having a high degree of association with control of and defense against the corn silk fly and phorid fly provides one of ordinary skill in the art the means for testing and identifying the presence of the genes responsible for controlling and defending against the corn silk fly and phorid fly in maize plants. The ability to test for and identify these genes is highly useful and advantageous to plant breeders seeking to develop maize plant lines that control for and defend against the corn silk fly and phorid fly.

Sources of Materials and Equipment

All of the materials and equipment that are employed in the methods and used for producing the products of the invention are commercially available from sources known to those having ordinary skill in the art. The initial seed sources were from the Corn Host Plant Resistance Unit at Mississippi State, MS and from A&C's commercial sweet corn breeding program. RAPiD Genomics's "Capture-Seq" genotyping method was utilized to identify the SNPs. Capture-Seq is a commercial service provided by RAPiD Genomics.

Seed Deposits of Parental Inbred Lines and Initial Hybrids

Because seed is living material, and must be produced over time, there are only limited quantities of the inbred lines 1115, 1118, and 1150 available for deposit at the present time. There are also limited quantities of maize hybrids containing one or more of the foregoing parental inbred lines available for deposit. For these reasons, seed deposits have been made with the American Type Culture Collection (ATCC) in the following amounts: ATCC Patent Deposit Designations PTA-124546 (AC 266Y) (2,000 seeds), PTA-124547 (AC 274YST) (2,000 seeds), PTA-124548 (NBD 01) (2,000 seeds), PTA-124549 (NBD 02) (2,000 seeds) and PTA-124550 (NBD 03) (200 seeds). The amounts deposited will be supplemented after seed increases are available in the future.

While the present invention has been described herein with specificity, and with reference to certain preferred embodiments thereof, those of ordinary skill in the art will recognize numerous variations, modifications and substitutions of that which has been described which can be made, and which are within the scope and spirit of the invention. It is intended that all of these modifications and variations be within the scope of the present invention as it is described and claimed herein, and that the invention be limited only by the scope of the claims which follow, and that such claims be interpreted as broadly as is reasonable.

What is claimed is:

1. A maize plant, plant material or seed modified through breeding comprising a quantitative trait locus region linked to one or more genes selected from the group consisting of SEQ ID NO: 1, SEQ ID NO: 2, SEQ ID NO: 3, SEQ ID NO: 4, and SEQ ID NO: 5 that controls or defends against corn silk fly and phorid fly, wherein the maize plant, plant material or seed does not require the use of chemical pesticides or insecticides for said control or defense, and wherein the ear and kernel have a damage rating of less than 2.

2. A maize plant, plant material or seed modified through breeding comprising a quantitative trait locus region linked to one or more genes selected from the group consisting of SEQ ID NO: 1, SEQ ID NO: 2, SEQ ID NO: 3, SEQ ID NO: 4, and SEQ ID NO: 5 that controls or defends against corn silk fly and phorid fly, wherein the maize plant, plant material or seed does not contain genes that have been transgenically introduced from a source outside a maize genome into maize plants, plant materials or seeds for said control or defense, and wherein the ear and kernel have a damage rating of less than 2.

3. The maize plant, plant material or seed of claim 1, wherein the maize plant, plant material or seed is a hybrid maize plant, plant material or seed.

4. The maize plant, plant material or seed of claim 2, wherein the maize plant, plant material or seed is a hybrid maize plant, plant material or seed.

5. The maize plant, plant material or seed of claim 1, wherein the maize plant, plant material or seed is *Zea mays*, convar *saccharata* var. *rugosa*.

6. The maize plant, plant material or seed of claim 2, wherein the maize plant, plant material or seed is *Zea mays*, convar *saccharata* var. *rugosa*.

\* \* \* \* \*